US010969536B2

(12) United States Patent
Zagatsky et al.

(10) Patent No.: US 10,969,536 B2
(45) Date of Patent: Apr. 6, 2021

(54) THERMALLY CONTROLLED ILLUMINATION DEVICES

(71) Applicant: Invuity, Inc., San Francisco, CA (US)

(72) Inventors: Vladimir Zagatsky, San Francisco, CA (US); Fernando Erismann, New York, NY (US); Alex Vayser, Mission Viejo, CA (US)

(73) Assignee: Invuity, Inc., San Francisco, CA (US)

( * ) Notice: Subject to any disclaimer, the term of this patent is extended or adjusted under 35 U.S.C. 154(b) by 145 days.

(21) Appl. No.: 16/160,269

(22) Filed: Oct. 15, 2018

(65) Prior Publication Data

US 2019/0049655 A1 Feb. 14, 2019

Related U.S. Application Data

(63) Continuation of application No. 14/939,825, filed on Nov. 12, 2015, now abandoned.
(Continued)

(51) Int. Cl.
*A61B 1/00* (2006.01)
*A61B 1/07* (2006.01)
(Continued)

(52) U.S. Cl.
CPC ........ *G02B 6/0085* (2013.01); *A61B 1/00167* (2013.01); *A61B 1/07* (2013.01);
(Continued)

(58) Field of Classification Search
CPC .... G02B 6/0085; G02B 6/002; G02B 6/0055; G02B 23/2469; G02B 23/2476; A61B 90/30; A61B 90/361; A61B 1/00167; A61B 1/07; A61B 1/00105; A61B 1/0623; A61B 1/267; A61B 1/303; A61B 1/32; A61B 17/02; A61B 17/0206; A61B 17/0293; A61B 17/3421; A61B 2017/00734;
(Continued)

(56) References Cited

U.S. PATENT DOCUMENTS 3,417,746 A 12/1968 Moore et al.
3,638,644 A 2/1972 Reick
(Continued)

OTHER PUBLICATIONS

International Search Report and Written Opinion dated Feb. 2, 2016 for PCT Application No. US2015/60470.

*Primary Examiner* — Pedro Philogene
(74) *Attorney, Agent, or Firm* — McDonnell Boehnen Hulbert & Berghoff LLP

(57) ABSTRACT

An illumination element has a light input section, a light transmitting section, and a light output section. The light input section is optically coupled to a proximal section of the light transmitting section and inputs light into the illumination element. The light transmitting section transmits the light by total internal reflection or by other transmission means. The light output section is adjacent a distal section of the light transmitting section which has a light extraction area from which the light exits with an energy density. The light extraction area comprises a bore extending at least partially inward into a distal end of the light output section. A plurality of optical structures is disposed on an inner wall of the bore. The optical structures are configured to extract light from the light output section and direct it toward the surgical field.

19 Claims, 38 Drawing Sheets

Related U.S. Application Data

(60) Provisional application No. 62/078,729, filed on Nov. 12, 2014.

(51) Int. Cl.
*A61B 90/00* (2016.01)
*A61B 90/30* (2016.01)
*A61M 1/00* (2006.01)
*F21V 8/00* (2006.01)
*G02B 23/24* (2006.01)

(52) U.S. Cl.
CPC .............. *A61B 90/30* (2016.02); *A61B 90/361* (2016.02); *A61M 1/0031* (2013.01); *G02B 6/002* (2013.01); *G02B 6/0055* (2013.01); *G02B 23/2469* (2013.01); *G02B 23/2476* (2013.01); *A61M 1/008* (2013.01); *A61M 2205/587* (2013.01)

(58) Field of Classification Search
CPC ....... A61B 2019/5206; A61B 19/5202; A61M 1/0031; A61M 1/008; A61M 2205/587; A61L 29/041
USPC ............. 600/284–249; 264/1.24; 385/14, 15, 385/114, 123–128, 141–146
See application file for complete search history.

(56) References Cited

U.S. PATENT DOCUMENTS

| | | | |
|---|---|---|---|
| 3,641,332 A | 2/1972 | Reick et al. | |
| 4,337,763 A * | 7/1982 | Petrassevich | A61B 1/32 600/210 |
| 4,732,448 A | 3/1988 | Goldenberg | |
| 4,733,332 A | 3/1988 | Yamashita et al. | |
| 4,763,969 A | 8/1988 | Khoe et al. | |
| 4,805,984 A | 2/1989 | Cobb, Jr. | |
| 4,806,289 A | 2/1989 | Laursen et al. | |
| 4,807,599 A | 2/1989 | Robinson et al. | |
| 4,979,798 A | 12/1990 | Lagakos et al. | |
| 5,005,944 A | 4/1991 | Laakmann et al. | |
| 5,027,259 A | 6/1991 | Chujko | |
| 5,050,946 A | 9/1991 | Hathaway et al. | |
| 5,109,465 A | 4/1992 | Klopotek | |
| 5,213,092 A | 5/1993 | Uram | |
| 5,428,484 A | 6/1995 | Baker | |
| 5,588,952 A | 12/1996 | Dandolu | |
| 5,651,783 A | 7/1997 | Reynard | |
| 5,882,194 A | 3/1999 | Davis et al. | |
| 5,931,670 A | 8/1999 | Davis | |
| 6,010,450 A | 1/2000 | Perkins | |
| 6,039,687 A | 3/2000 | Storz | |
| 6,056,426 A | 5/2000 | Jenkins | |
| 6,185,356 B1 | 2/2001 | Parker et al. | |
| 7,467,875 B1 | 12/2008 | Rama | |
| 8,088,066 B2 | 1/2012 | Grey et al. | |
| 8,348,838 B1 | 1/2013 | Khurgin et al. | |
| 8,409,088 B2 | 4/2013 | Grey et al. | |
| 8,876,709 B2 | 11/2014 | Vayser et al. | |
| 8,948,560 B1 | 2/2015 | Wach | |
| 9,114,202 B1 | 8/2015 | Huttner | |
| 9,510,737 B2 | 12/2016 | Vayser et al. | |
| 9,510,847 B2 * | 12/2016 | Auld | A61B 17/28 |
| 9,610,130 B2 | 4/2017 | Vayser et al. | |
| 10,463,444 B2 * | 11/2019 | Davis | A61B 90/35 |
| 2001/0012429 A1 | 8/2001 | Wach et al. | |
| 2002/0191928 A1 | 12/2002 | Carter et al. | |
| 2003/0032860 A1 | 2/2003 | Avni et al. | |
| 2003/0060680 A1 | 3/2003 | Wendlandt | |
| 2003/0163030 A1 | 8/2003 | Arriaga | |
| 2003/0187331 A1 | 10/2003 | Faludi et al. | |
| 2004/0236231 A1 | 11/2004 | Knighton et al. | |
| 2005/0165283 A1 | 7/2005 | Hestad et al. | |
| 2006/0069314 A1 | 3/2006 | Farr | |
| 2006/0158746 A1 | 7/2006 | Lim et al. | |
| 2006/0171632 A1 | 8/2006 | Dixon | |
| 2006/0195165 A1 | 8/2006 | Gertner et al. | |
| 2006/0211918 A1 | 9/2006 | Lieponis | |
| 2006/0242884 A1 | 11/2006 | Talieh | |
| 2006/0256575 A1 | 11/2006 | Vayser | |
| 2006/0276693 A1 * | 12/2006 | Pacey | A61B 1/00142 600/188 |
| 2007/0179430 A1 | 8/2007 | Smith et al. | |
| 2007/0213590 A1 | 9/2007 | Squicciarini | |
| 2007/0293729 A1 | 12/2007 | Grey et al. | |
| 2008/0228085 A1 | 9/2008 | Jenkins et al. | |
| 2008/0294002 A1 | 11/2008 | Xie | |
| 2009/0036744 A1 | 2/2009 | Vayser | |
| 2009/0187072 A1 | 7/2009 | Manohara et al. | |
| 2009/0221991 A1 | 9/2009 | Lieponis | |
| 2009/0292168 A1 | 11/2009 | Farr | |
| 2009/0318758 A1 | 12/2009 | Farr et al. | |
| 2009/0326572 A1 | 12/2009 | Peh et al. | |
| 2010/0010312 A1 | 1/2010 | Gilad et al. | |
| 2010/0030033 A1 | 2/2010 | Farley et al. | |
| 2010/0041955 A1 | 2/2010 | Grey et al. | |
| 2010/0080016 A1 | 4/2010 | Fukui et al. | |
| 2010/0125170 A1 | 5/2010 | Sugimoto | |
| 2010/0210911 A1 | 8/2010 | Shimotsu | |
| 2011/0069278 A1 | 3/2011 | Gueder | |
| 2011/0112376 A1 | 5/2011 | Vayser et al. | |
| 2011/0230722 A1 | 9/2011 | Kudo et al. | |
| 2011/0282160 A1 | 11/2011 | Bhadri et al. | |
| 2012/0002422 A1 | 1/2012 | Lia et al. | |
| 2012/0041268 A1 * | 2/2012 | Grey | A61B 1/0623 600/199 |
| 2012/0059224 A1 | 3/2012 | Wellen et al. | |
| 2012/0099112 A1 | 4/2012 | Alphonse et al. | |
| 2012/0184971 A1 | 7/2012 | Zentgraf et al. | |
| 2013/0012783 A1 * | 1/2013 | Vayser | A61B 1/0017 600/249 |
| 2013/0128223 A1 | 5/2013 | Wood et al. | |
| 2013/0197317 A1 | 8/2013 | Daniel et al. | |
| 2013/0274548 A1 | 10/2013 | Fels et al. | |
| 2013/0331654 A1 | 12/2013 | Hermanowski | |
| 2014/0088371 A1 | 3/2014 | Vayser et al. | |
| 2014/0107496 A1 | 4/2014 | Hellstrom et al. | |
| 2014/0152789 A1 | 6/2014 | Hu et al. | |
| 2015/0078031 A1 | 3/2015 | Komazaki et al. | |
| 2015/0119650 A1 | 4/2015 | Hacker et al. | |
| 2015/0126874 A1 | 5/2015 | Lee et al. | |
| 2015/0277015 A1 | 10/2015 | Lu et al. | |
| 2016/0015467 A1 | 1/2016 | Vayser et al. | |
| 2016/0058383 A1 | 3/2016 | Hellstrom et al. | |
| 2016/0213233 A1 | 7/2016 | Vayser et al. | |
| 2016/0256705 A1 | 9/2016 | Webler, Jr. et al. | |
| 2017/0095310 A1 | 4/2017 | Vayser et al. | |
| 2017/0095311 A1 | 4/2017 | Vayser et al. | |
| 2017/0100022 A1 | 4/2017 | Vayser et al. | |
| 2017/0100023 A1 | 4/2017 | Vayser | |

* cited by examiner

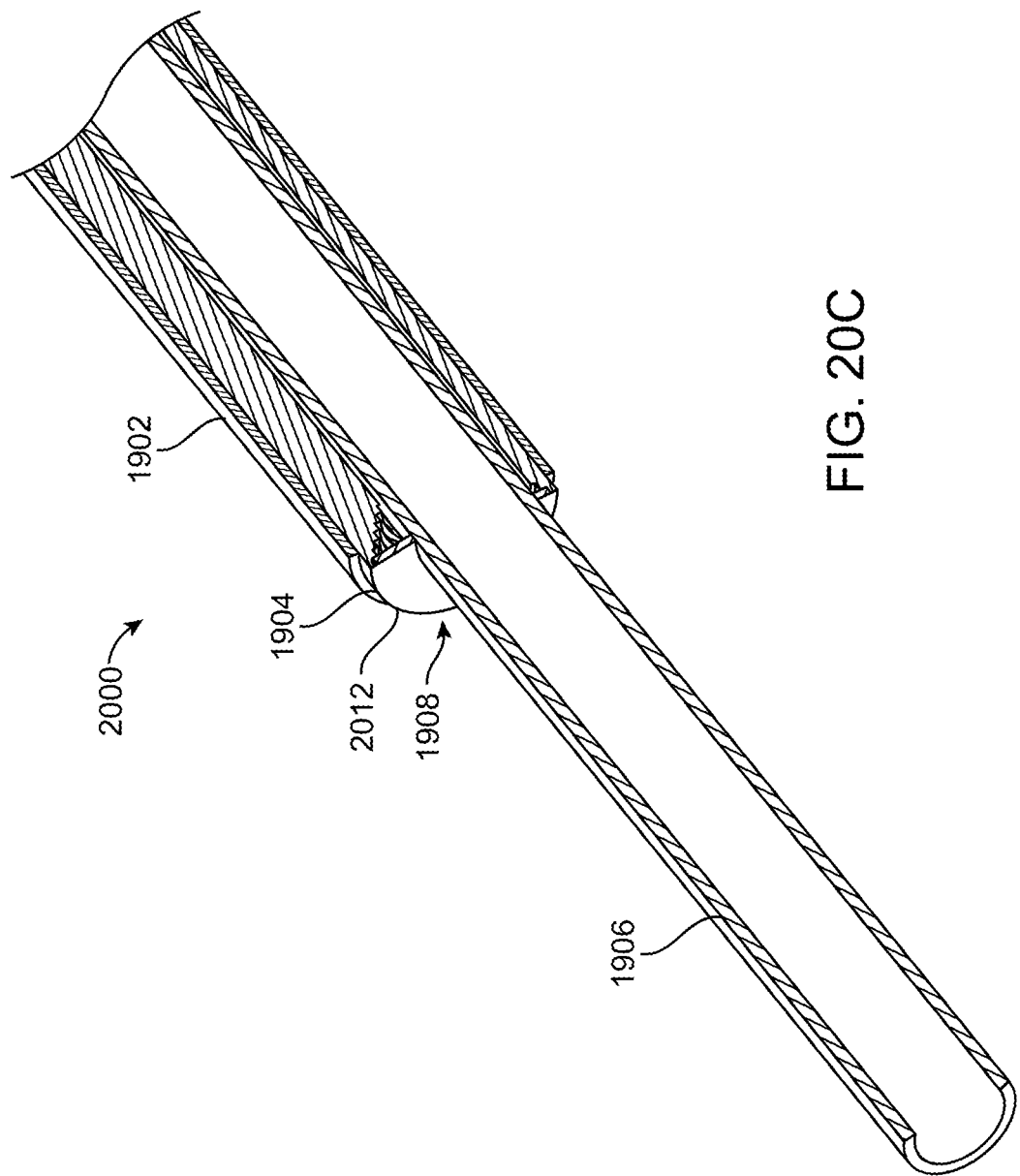

THERMALLY CONTROLLED ILLUMINATION DEVICES

CROSS-REFERENCE

The present application is a continuation application of U.S. patent application Ser. No. 14/939,825, filed Nov. 12, 2015, which is a non-provisional of, and claims the benefit of, U.S. Provisional Patent Application No. 62/078,729 filed Nov. 12, 2014; each of which applications is entirely incorporated herein by reference.

The present application is related to U.S. patent application Ser. No. 14/487,645 filed Sep. 16, 2014 which is a non-provisional of, and claims the benefit of U.S. Provisional Patent Application No. 61/878,395 filed Sep. 16, 2013; the entire contents of which are incorporated herein by reference.

BACKGROUND

1. Field of the Invention

The present invention generally relates to medical devices and methods, and more particularly relates to illuminated surgical instruments such as illuminated surgical retractors and handheld instruments such as illuminated suction devices. One of skill in the art will appreciate that these examples are not intended to be limiting and that other illuminated instruments or tools are also contemplated.

There are various surgical devices in the market that provide illumination to a surgical field. A number of these devices include a light guide which includes either a bundle of optical fibers or a single fiber. In the operating room, modern light sources are used to produce a tremendous amount of illumination intensity. This energy is coupled into these illumination products, which transmit the light over a distance and then the energy is output onto the surgical surface.

In certain circumstances, these devices can create a thermal danger to the patient, the user, or the equipment being used. When all the optical energy from a fiber bundle is focused on a patient, tissue can dry out, and the heat generated can also result in burns. Surgical drapes have been reported to melt and catch on fire in the operating room. During surgical procedures, blood, other debris, or surgical drapes may obstruct the device and block light output. Obstructing light creates several issues. The first is reduction of illumination on the field, thus minimizing the visual acuity of the task. This obviously can affect the efficiency of the procedure. A more critical issue however is thermal buildup on the section of the illumination device which is obstructed. Since the light cannot exit, it converts to heat as it is blocked. Blood, for example, coagulates at an average temperature of 40° C., so as it coagulates on the surface of the illumination device it will block light output minimizing the amount of light exiting the device. The increased energy density will also further heat up the device. Fiber bundles are often fabricated from glass which may not be affected by this, but adhesives used in the fiber bundle assembly may be damaged from the heat, and when the fiber bundles are fabricated from polymers, the fibers may heat up and melt or exceed the glass transition temperature and deform. Therefore it would be desirable to provide illuminated surgical instruments that are able to control heat generated so as to avoid damaging the illuminated surgical instrument, as well as avoiding harming the patient or operator. In the example of the surgical drape, if the drape is obstructing the illumination element, the energy density on the drape is much higher for several reasons. As mentioned earlier the illumination element heats up if the drape is actually touching the illumination element. Even if the drape is merely very close to the illumination element and there is air space, the energy density of light being absorbed by the drape is so high that it will melt the drape when compared to a drape that is disposed further away from the illumination element and the light is dispersed over a larger area on the drape.

Therefore, it would be desirable to provide a device that has a low energy density output. Energy density may be controlled by increasing the surface area from which the light is delivered, thereby reducing the heat generated. However, an increase in surface area may increase the overall profile of the surgical device. This may be undesirable because a larger surgical device may occupy too much space in the surgical field, thereby requiring a larger incision which is undesirable. Thus, with ever decreasing surgical incision sizes, it would also be advantageous to provide an illuminated surgical instrument with a low profile so as to avoid obstructing the surgical field.

At least some of these objectives will be satisfied by the devices and methods disclosed below.

2. Description of the Background Art

Illuminated surgical instruments may include illumination elements such as fiber optics, optical waveguides, or other means for providing the light. Optical waveguides and fiber optics are well known in the art.

SUMMARY

The present invention generally relates to medical devices and methods, and more particularly relates to medical and surgical instruments that can illuminate a surgical field. Even more particularly, such illuminated surgical and medical instruments are designed to control and manage their thermal properties during use so as to minimize or prevent melting or other damage to the instrument, the surgical field, and harm to the patient or operator.

In a first aspect of the present invention, an illumination element for illuminating a surgical field in a patient may comprise a light input section, a light transmitting section, and light output section. The light input section is for inputting light into the illumination element, and the light transmitting section transmits light therethrough, preferably by total internal reflection or by other means such as by using coatings on the illumination element. The light input section is optically coupled to a proximal section of the light transmitting section. The light output section is adjacent a distal section of the light transmitting section, and comprises a light extraction area with light exiting the light output section with an energy density. The light extraction area is large enough to maintain the energy density at a level that prevents melting or other damage of the illumination element or burning of the patient or operator, and the light extraction area has a low profile configured to avoid obstructing access to the surgical field and visualization thereof.

The light output section may be tapered, either flat or conically tapered, and the light output section may comprise an upper surface and a flat planer lower surface. The upper surface may be angled relative to the flat planer lower surface. The upper surface may form an angle of 30 degrees or less relative to the flat planar lower surface. In alternative embodiments, the upper surface or the lower surface may be curved.

The light input section may have a cross-sectional area, and the extraction area may be at least twice the input cross-sectional area. The light extraction area may be balanced so as to provide uniform light output therefrom. Balancing may be accomplished with light extraction surface features such as lenslets, prisms, stair steps, or other features which help control and direct the extracted light. The light input cross-sectional area may be in a plane that is perpendicular or otherwise transverse to the plane of the light extraction area.

The illumination element may be an optical waveguide and may further comprise cladding disposed over at least a section of the light input section, light transmitting section, or the output section. The cladding may have an index of refraction in the range from about 1 to about 1.5.

The illumination element or optical waveguide may further comprise a surgical instrument coupled to the light input section, the light transmitting section, or the light output section. The surgical instrument may comprise a suction tube or a surgical retractor blade. The suction tube or the surgical instrument may comprise interchangeably sized tips.

The illumination element may comprise an optical waveguide, and light input into the illumination element may be transmitted through the transmitting section by total internal reflection, or by other means for transmission.

In another aspect of the present invention, a method for illuminating a surgical field in a patient comprises providing an illumination element such as an optical waveguide having a light input section, a light transmitting section, and a light output section, and inputting light from an external source into the illumination element or the optical waveguide via the light input section. The method also comprises transmitting the light through the light transmitting section, and this may be accomplished via total internal reflection or another light transmission means, and extracting the light from the light output section. The method also comprises maintaining energy density of the light extracted from the light output section at a level that prevents melting of the illumination element which may be an optical waveguide or burning of the patient or operator, and illuminating the surgical field with the extracted light.

The method may comprise advancing the illumination element or optical waveguide toward the surgical field without obstructing the surgical field. Maintaining the energy density may comprise providing the input section with a cross-sectional area, and providing the light output section with a light extraction area, wherein the light extraction area is at least twice the input section cross-sectional area. The cross-sectional area of the input section may be in a plane that is perpendicular or otherwise transverse to the plane in which the light extraction area is disposed.

The method may further comprise balancing the extracted light so as to provide uniform illumination of the surgical field. This may be accomplished by providing extraction surface features on the illumination element such as lenslets, prisms, or stair steps which help control and direct the extracted light. The method may also comprise providing a suction tube or a surgical instrument coupled to the light input section, the light transmitting section, or the light output section of the illumination element or optical waveguide. The method may further comprise interchanging interchangeable instrument tips with either the suction tube or the surgical instrument.

In some embodiments, the illumination element comprises an optical waveguide and light is transmitted through the transmitting section via total internal reflection or by other transmission means.

In another aspect of the present invention, an illumination element for illuminating a surgical field in a patient comprises a light input section for inputting light into the illumination element, a light transmitting section, wherein the inputted light is transmitted through the light transmitting section, and wherein the light input section is optically coupled to a proximal section of the light transmitting section, and a light output section, wherein the light output section is adjacent a distal section of the light transmitting section, and wherein the light output section comprises a bore extending at least partially inward into a distal end of the light output section, and wherein a plurality of optical structures are disposed on an inner wall of the bore, the optical structures configured to extract light from the light output section and direct the extracted light toward the surgical field.

The bore may extend only partially inward into the light output section, and the bore may be a conically shaped bore. A window may be disposed over the bore and the window may be configured to prevent tissue or blood from entering the bore. Some of the plurality of optical structures may extend completely or only partially around the circumference of the bore.

The light extracted from the light output section may have an energy density, and wherein the light output section may have an extraction area large enough to maintain the energy density at a level that prevents melting of the illumination element or burning of the patient. The light input section may have a cross-sectional area and the extraction area may be larger than the light input cross-sectional area. In some embodiments, the extraction area may be at least twice as large as the light input area.

The illumination element may further comprise a layer of cladding disposed thereover and configured to minimize light loss therefrom. The cladding may have an index of refraction in the range from about 1 to about 1.5. The illumination element may further comprise an instrument such as a surgical instrument, a tool, or any other apparatus used to perform a task, and the illumination element may be disposed over the instrument. The instrument may be a suction tube and the illumination element may be a non-fiber optic optical waveguide. A suction control mechanism may be fluidly coupled to the suction tube. Alternatively, the instrument may be a camera, a sensor, or any other tool. The light may be transmitted through the light transmitting section by total internal reflection (TIR). Light is preferably emitted distally from the illumination element in a symmetrical spot on the surgical field. The light may also be a non-symmetrical spot. A handle may be coupled to a proximal portion of the light input section.

In yet another aspect of the present invention, a method for illuminating a surgical field in a patient comprises providing an illumination element having a light input section, a light transmitting section, and a light output section; inputting light from a light source into the illumination source via the light input section, and transmitting the light transmitting section. The method also comprises extracting the light from the light output section, wherein extracting the light comprises extracting the light from a plurality of optical structures disposed on an inner surface of a conical bore in a distal portion of the illumination element; and illuminating the surgical field with the extracted light.

Extracting the light may comprise maintaining energy density of the extracted light at a level that prevents melting of the illumination element or burning of the patient. Maintaining the energy density may comprise providing the input section with a cross-sectional area, and providing the light output section with a light extraction area, wherein the light extraction area may be larger than the input section cross-sectional area. The light extraction area may be at least twice the input section cross-sectional area.

The method may further comprise providing an instrument such as a suction tube, retractor, or a surgical instrument, coupled to the illumination element. The method may also further comprise retracting tissue with the retractor, or removing fluid, tissue or debris from the surgical field with suction delivered by the suction tube. Transmitting the light may comprise transmitting the light through the light transmitting section via total internal reflection.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 20A-20C illustrate perspective views and a partial cross-section of yet another exemplary embodiment of an illuminated instrument.

DETAILED DESCRIPTION

Specific embodiments of the disclosed device and method will now be described with reference to the drawings. Nothing in this detailed description is intended to imply that any particular component, feature, or step is essential to the invention.

Figure 1:
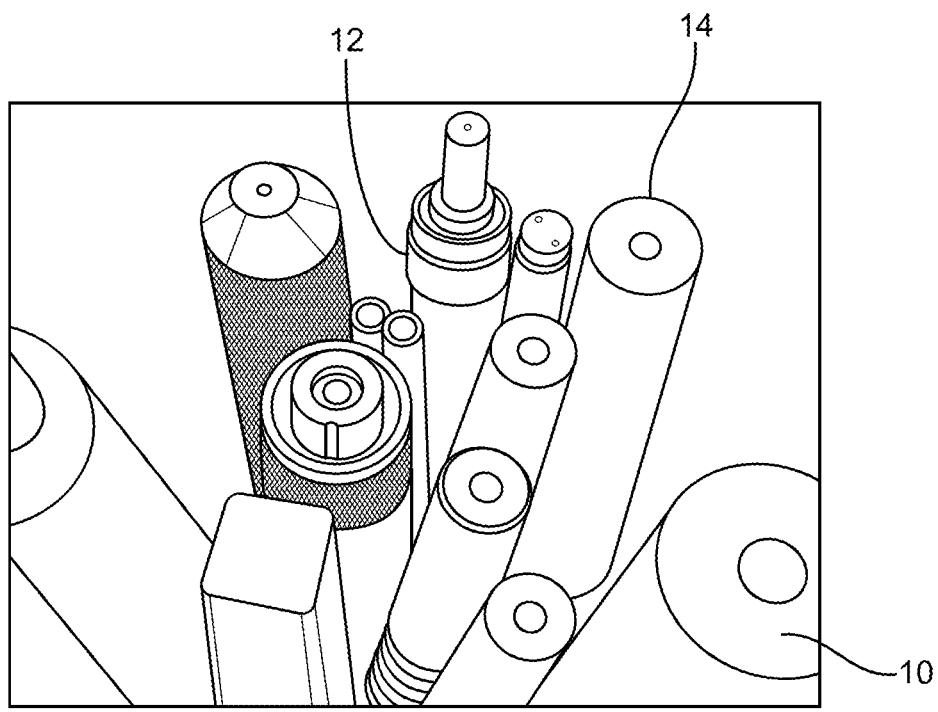
FIG. 1 illustrates typical fiber optic cables.

FIG. 1 illustrates typical fiber optic cables 10 which are often constructed with a barrel type connector 12 and have distal tips which are circular and flat 14. The reason they are cut flat is because when they are assembled, they are cut and polished. The angle of the distal tip of the fiber bundle dictates how much light will come out of the fiber and at what angle the light exits the fiber based on the material of the fiber and any air interface, a typical angle is approximately 6 degrees. The angle may be greater than 6 degrees, but efficiency starts to drop.

Fiber optic cables are often connected to external light sources, such as a 300 Watt xenon light source, which exhibits high power output. When the tip of the fiber is absolutely clean or unobstructed, the temperature of the tip remains at safe levels, however when the tip of the fiber optic cable is obstructed with absorbing media such as debris, blood or fluids or even blocked by a surgical drape or a patient's skin, the illumination energy density quickly converts to heat and the tip heats up. The temperature can rise to over 150° C. This temperature is high enough to cause a burn on a patient or the operator, or melt a surgical drape or even result in a fire. Since blood coagulates at a much lower temperature, it will "bake" on the tip greatly reducing the output. This causes less visibility to the surgical procedure for the surgeon thus potentially creating risk. As previously mentioned even if the illuminator is not blocked and there is an air gap, absorption by a drape or skin can still cause damage.

Another issue that the increased temperature can cause is damage to the illuminator. The increased temperature is unlikely to damage glass fibers, but it may melt plastic fibers. Also, any adhesives or polymer components used in the adjacent area may also melt or be damaged by the heat, regardless of whether the illuminator is glass or plastic.

Therefore, it would be desirable to provide illuminated instruments and devices that are better at controlling heat in order to avoid damage to the device or harming the patient or the operator. Such a device preferably maintains the power output while minimizing energy density. One solution is to increase the light output or extraction area. Energy density may be minimized by increasing the extraction area. However, an increase in extraction area can increase the instrument profile which can obstruct the surgical field. Therefore, the energy density is preferably minimized by increasing extraction area, while maintaining a low profile on the device, while at the same time taking into account the thermal conductivity of the device as well as its melting characteristics.

Figure 15:
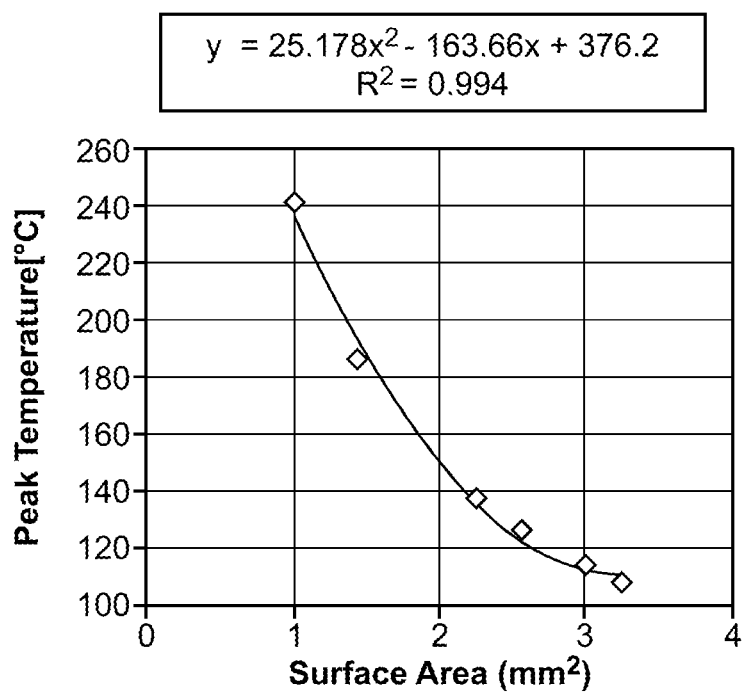
FIG. 15 illustrates the relationship between temperature and surface area in an illumination element.

To address this, one has to create a large output area that minimizes the thermal/energy density across that surface without compromising practicality of the device in surgical applications where it may be too obtrusive. FIG. 15 illustrates the relationship between peak device temperature and surface area in one particular embodiment of an illumination element (also referred to herein as an illuminator). Clearly, temperature decreases with increasing surface area, assuming there is a uniform light output. In particular, there is a significant decrease in temperature for a doubling of the surface area. This graph was generated with a cyclo olefin polymer (COP) waveguide with the surface covered by a 1 W thermal load. In another embodiment, with a large area for delivery of light, if 80% of the light is extracted from only 10% of the device area, this theory may not apply.

Figure 2:
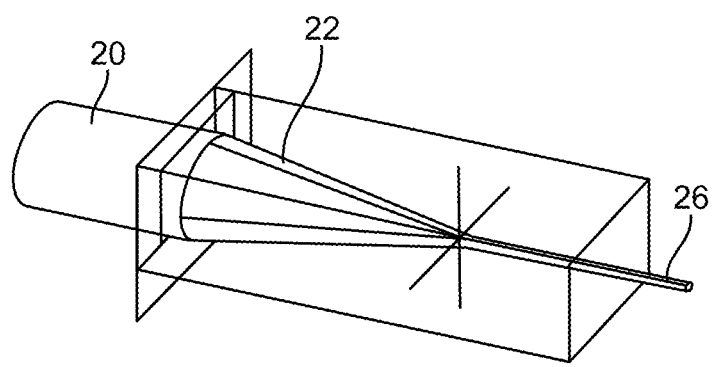
FIG. 2 illustrates a fiber optic with a tapered tip.

FIG. 2 illustrates a fiber bundle 26 having a plurality of flat tapered surfaces disposed around the circumference of the distal tapered region 22 so that the output end of the fiber bundle 20 has a larger output surface area than if the light simply exited the distal-most face of the fiber bundle. This spreads the output over a larger area, thereby keeping energy density lower and preventing overheating. However, this embodiment may not be ideal since the large profile of the bundle 20 may be too obstructive in a surgical field. This embodiment may be fabricated by polishing an outer surface of each fiber on the outer circumference of the bundle. Each outer surface may be polished into a flat planar region. The fibers in the center of the bundle may retain their preferably round configuration.

In order to provide an illumination element such as an optical waveguide that controls heat and provides a suitable profile, the present inventors disclose herein several exemplary embodiments of optical waveguides. Preferably, they may be fabricated using any suitable optical material, such as acrylic, polycarbonate, cyclo olefin polymer (COP), cyclo olefin copolymer (COC), or other materials used in the art. Still other embodiments may be fabricated from a silicone material that allows a malleable and flexible illumination element to be produced, and that can conform to the shape of the instrument to which it is paired. In some embodiments, the malleable illumination element may be pulled over the instrument like a glove, or the malleable illumination element may be disposed and pressed into a channel sized to receive the illumination element, the channel being disposed along the instrument. The optical waveguide is preferably coupled to the end of a fiber optic bundle (either releasably attached, fixedly attached (e.g. by bonding), or otherwise coupled thereto). Light is introduced into the optical waveguide from the fiber optic bundle and the light is then preferably transmitted along the waveguide by total internal reflection or by other light transmission principles (e.g. coatings), and the light is then extracted and delivered from a large area of the optical waveguide. The optical waveguide is preferably not a fiber optic. The optical waveguide may be a single unitary component that is preferably injection molded from a homogenous material. The optical waveguide preferably minimizes profile, reduces energy density and extracts light uniformly across the surface of the waveguide.

Figure 3:
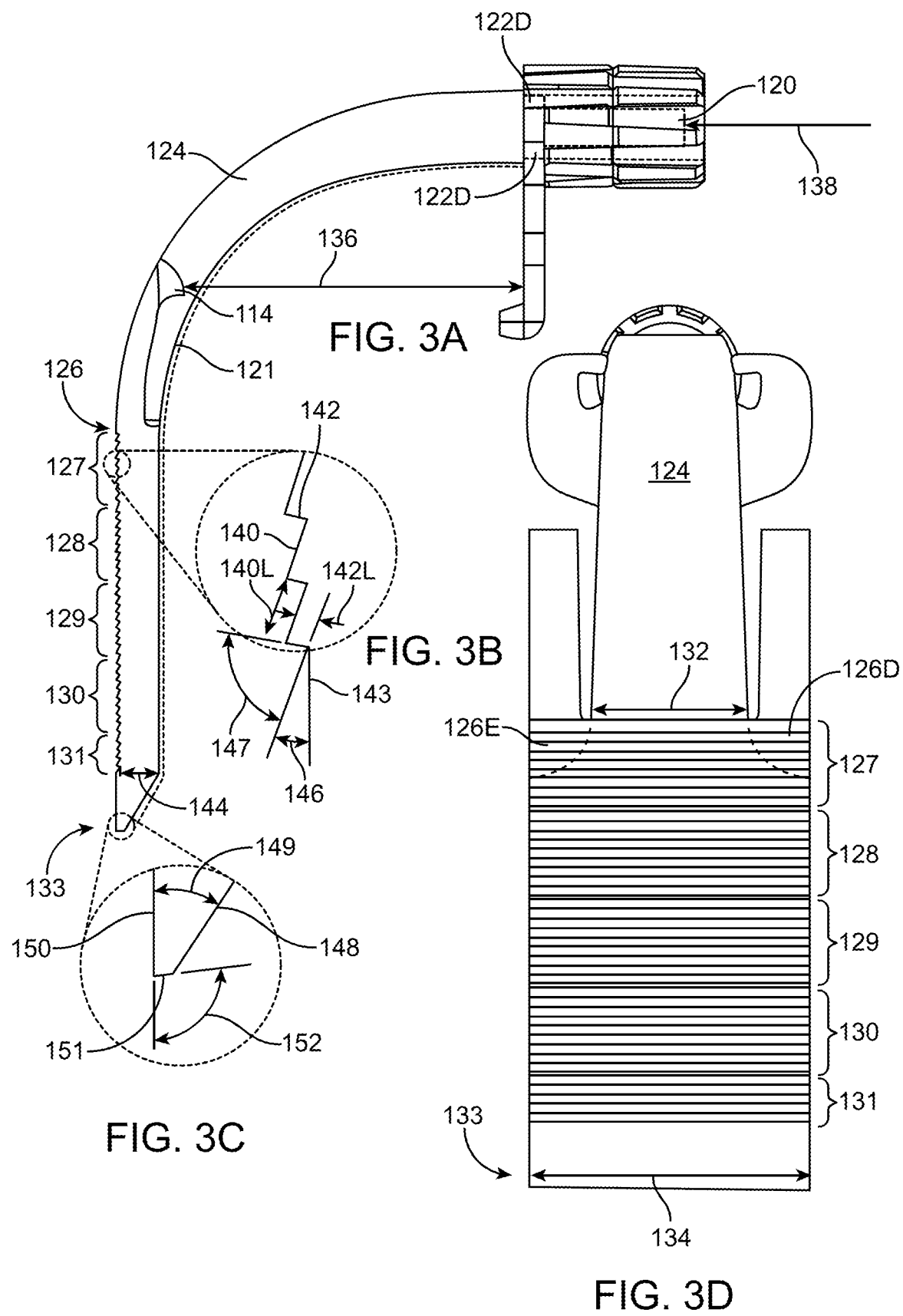
FIGS. 3A-3D illustrate an exemplary embodiment of an illumination element.

To achieve these goals, the extraction area is preferably at least twice the cross-sectional area of the input source for a non-tapered extraction area. The light input section of the illumination element such as an optical waveguide typically matches the cross-sectional area of the input source, therefore, the ratio of the extraction area to the cross-sectional area of the light input section is similarly at least 2:1. Thus, for example, if the input source is a 4 mm diameter cable, the input area is approximately 12.5 mm$^2$ and thus the extraction area is preferably at least 25 mm$^2$. The exemplary embodiment seen in FIGS. 3A-3D illustrate an illumination element such as an optical waveguide having an input 138 cross-sectional area that is at least two times smaller than the light extraction area 127-131. Additionally, the light extraction surface is parallel to the rear surface of the waveguide. The rear surface is substantially flat and planar. Additionally, the cross-sectional thickness of the input is larger than the thickness of the extraction area in order to ensure that profile at the extraction area remains low. Light output from the extraction area is also balanced. The surface features can vary dimensionally from the proximal part of the extraction zone to the distal part of the extraction zone so that light output does not vary across the surface and is uniformly delivered to the surgical field. For example each surface feature may include a stair step structure having a step face and a ramp face. An angle is disposed therebetween. The length of the step face or the ramp face may change (e.g. increase or decrease) between various stair steps in order to provide uniform illumination. Thus, the angle between the step face and ramp face may change (e.g. increase or decrease) between different stair steps in the extraction area. Additional details on the optical waveguide in FIG. 3 are disclosed in U.S. Pat. No. 8,088,066; the entire contents of which are incorporated herein by reference.

Figure 4:
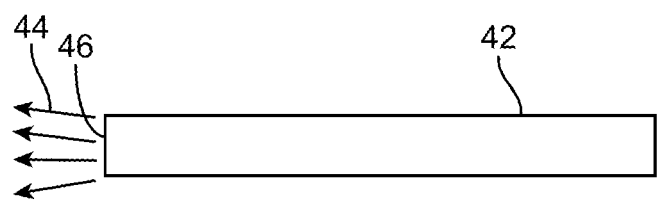
FIG. 4 illustrates an illumination element with a blunt distal tip.
Figure 5:
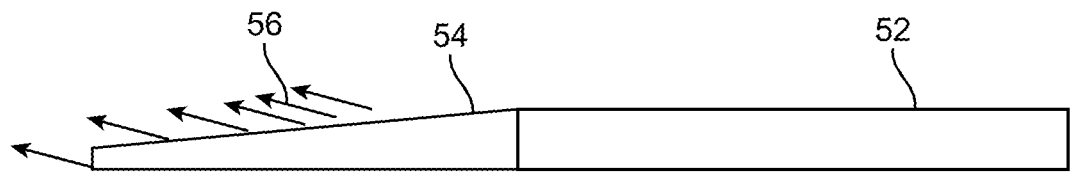
FIG. 5 illustrates an illumination element with a tapered tip.
Figure 6:
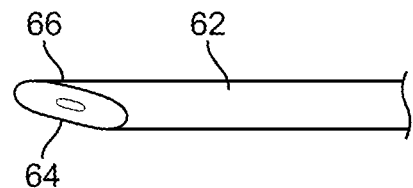
FIG. 6 illustrates a perspective view of an illumination element with a tapered tip.

FIG. 4 illustrates a typical illumination element such as waveguide 42 having a blunt distal end 46 that is orthogonal to the longitudinal axis of the waveguide 42. Light 44 travels through the waveguide and exits the distal end 46. Thus, the energy density is distributed over the surface area of the distal end 46. Other waveguides may have surface features such as microstructures on an outer surface to extract light laterally from the waveguide, as seen in FIG. 3. This allows the energy density to be distributed over a larger surface area. Using a tapered surface as seen in FIG. 5 allows an even larger surface area to created for light delivery, thereby further decreasing energy density. In FIG. 5, the illumination element is a waveguide 52 including a tapered tip 54 from which the light 56 is delivered. The tapered surface creates a larger surface area than that provided by a flat horizontal planar surface. FIG. 6 illustrates a perspective view of the tapered distal tip 64 of waveguide 62 with a flat and oval shaped 66 surface area for delivering the light. The ratios of input cross-sectional area and output cross-sectional area may be applied to any of the embodiments of illumination elements disclosed herein.

Figure 18A:
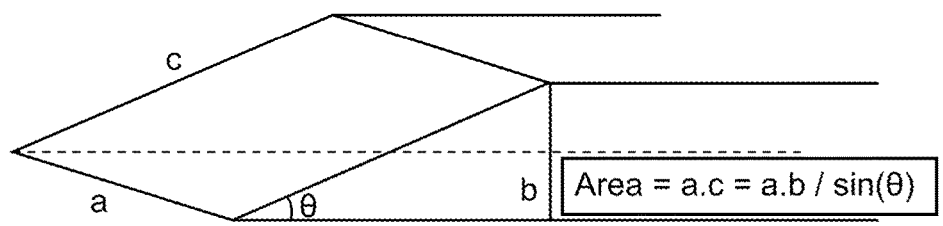
FIGS. 18A-18B illustrate how stair steps create additional surface area relative to a tapered surface.
Figure 18B:
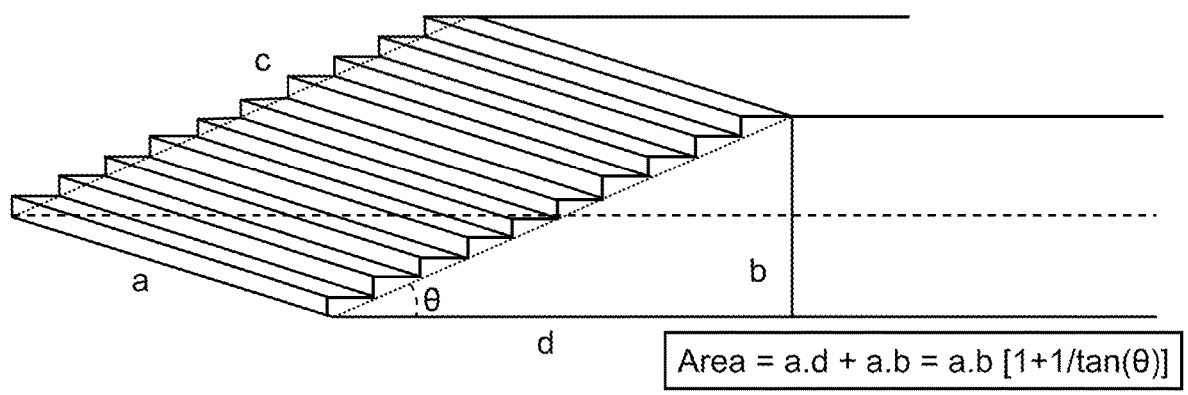

FIGS. 18A-18B illustrate how the surface area of a tapered surface may further be increased. FIG. 18A illustrates the surface area for light extraction in a simple tapered illumination element such as a waveguide. In FIG. 18B, the surface area for light extraction has been increased by adding stair stepped facets on the ramp, thereby adding additional surface area. The angle $\Theta$ is still preferably a maximum of 30 degrees in order to have at least a doubling of the area relative to the input cross-sectional area.

Figure 7:
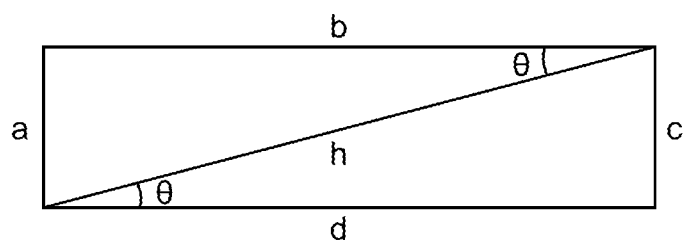
FIG. 7 illustrates increased surface area of a tapered tip relative to a flat horizontal tip.
Figure 16:
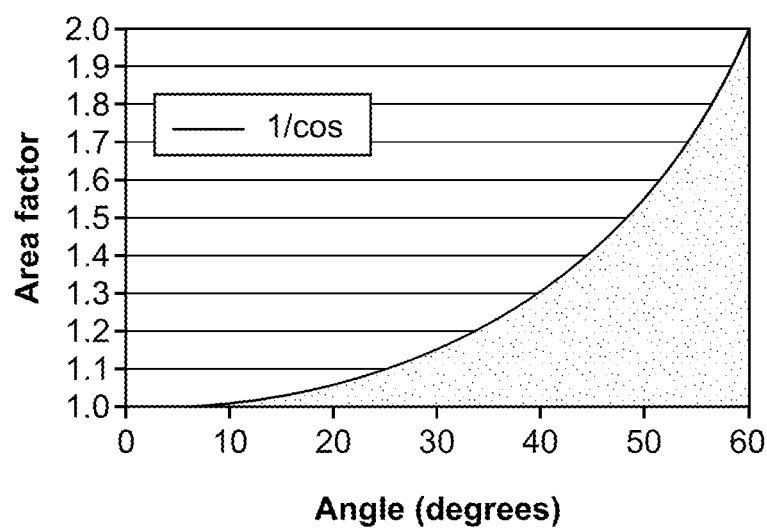
FIG. 16 illustrates the relationship between surface area and taper angle.

FIG. 16 illustrates the relationship between light output surface area and the taper angle. The angle in FIG. 16 is graphed as 90-$\Theta$, where $\Theta$ is measured between the tapered surface and the flat planar back surface. FIG. 16 clearly shows that surface area increases with taper angle. FIG. 7 illustrates why a tapered surface provides a larger surface area compared to a flat planer horizontal surface. A flat planar illumination element such as a waveguide tip is defined by a-b-c-d, and light exits either surface a or surface b. Clearly surface b has a larger surface area than surface a. However, if a tapered tip is formed on the waveguide defined by c-d-h thereby forming a beveled tip, then the surface h becomes the extraction area, and has a length that can be calculated using basic trigonometry. Thus, $h = c/\sine \Theta$, or $h = d/\cosine \Theta$ Since d=b, it is clear that h is longer than b when $\Theta$ is greater than zero degrees, thus the tapered tip provides a larger area for light extraction and delivery. Therefore the energy density is lower with a tapered tip relative to a flat planar vertical tip such as when light exits the distal-most face of a fiber. Similar calculations can be used to determine that the taper angle must be a maximum of 30 degrees (relative to the horizontal surface b or d) in order to create a surface that has a surface area at least twice that of the input surface area. The smaller the angle $\Theta$, the more gradual the ramp angle, therefore the longer the beveled tip will be, increasing length and the corresponding extraction area.

Figure 17A:
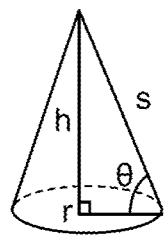
FIGS. 17A-17B illustrate the relationship between a conical taper angle and the surface area.
Figure 17B:
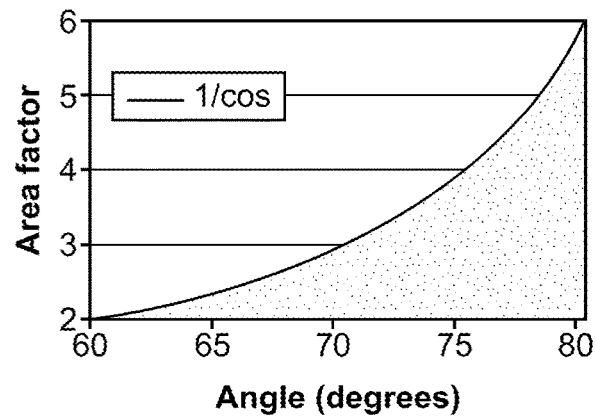

FIG. 17A illustrates basic cone geometry, the cone having a base with radius r, a height h, and an outer surface s. Angle theta is defined between s and r. FIG. 17B illustrates the relationship between surface area and the angle $\Theta$ in the cone. Again, changing a conical taper changes the angle $\Theta$ which can have a significant impact on surface area. The conical taper may extend entirely around the circumference of the cone, or the taper may only be on a portion of the cone. The taper may be symmetrical or non-symmetrical. The taper may be on one or more portions of the cone. Taper angles may be the same or different if more than one tapered portion exists. For example, a top portion of the cone may be tapered at one angle, and a bottom portion of the cone may be tapered at another angle. In an alternative embodiment, a top portion of the cone may have a taper angle and the bottom portion of the cone may be missing altogether.

Figure 8:
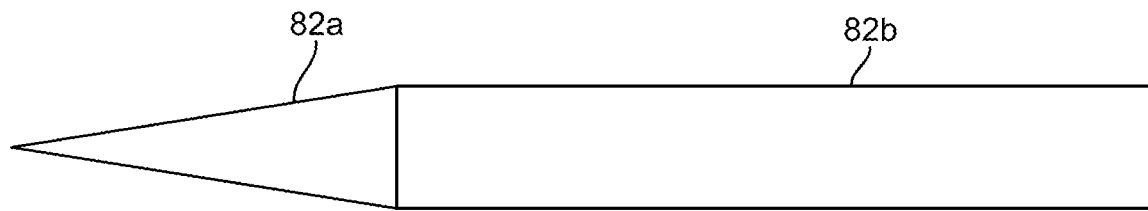
FIG. 8 illustrates an illumination element having a conically tapered tip.

FIG. 8 illustrates another means for reducing profile and creating a larger light extraction area by forming a conical taper 82a on the distal section of the illumination element, here a waveguide 82b. The cone may partially or completely surround the surgical instrument. Exemplary use of this includes an illuminated suction device that is completely formed from waveguide material. A central hollow bore (not illustrated) in the waveguide serves as a suction channel and allows suction to be applied without requiring a separate suction tube.

Figure 9:
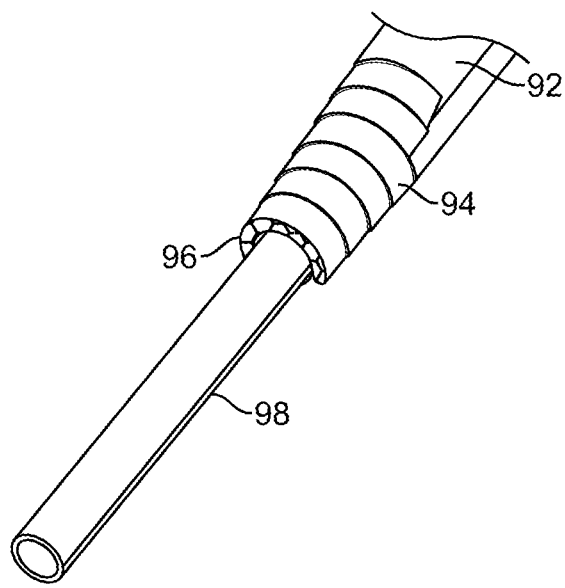
FIG. 9 illustrates still another exemplary embodiment of an illumination element with increased light extraction surface area.
Figure 35:
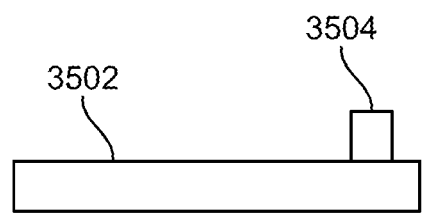
FIG. 35 illustrates an illumination element coupled with an instrument.

FIG. 9 shows another embodiment of an illuminated surgical instrument having an increased light extraction surface area for controlling heat in the device. An illumination element such as an optical waveguide 92 is coupled to a suction tube 98. The waveguide 92 has a tapered region that tapers into different planes 94, thereby forming multiple stair steps or terraces. The planes may be the same or different. This design allows a long taper on the top and a shorter taper on the sides to create a more tailored light extraction mechanism. This creates the desired larger surface area for light extraction, as well as helps to keep the profile minimized. Surface features such as microstructures may be disposed on the tapered region to help extract and direct light from the optical waveguide. The surface features may be flat such as prisms, or other planar facet features, or the surface features may be radiused to further control the light being extracted from the waveguide. The surface features may be uniform or they may be each unique in order to extract and deliver the light as required by the application. Any combination of surface features may be used, such as lenslets 96 on the distal-most tip of the waveguide. The lenslets may overlap with one another so that light projected therefrom onto the surgical field also overlaps thereby providing more uniform illumination of the surgical field. This embodiment with a suction tube is not intended to be limiting and one of skill in the art appreciates that an illumination element may be coupled to any number of other surgical handheld instruments. Therefore, in still other embodiments, an illumination element may be coupled to any number of other handheld surgical instruments such as retractors, probes, electrosurgery instruments, a camera or other sensor instruments, etc. FIG. 35 illustrates an illumination element 3502 which may be any of the illumination elements described herein coupled to any other instrument 3504 which may be any of the other instruments described herein such as those described above in FIG. 9, or any other instrument.

Figure 10:
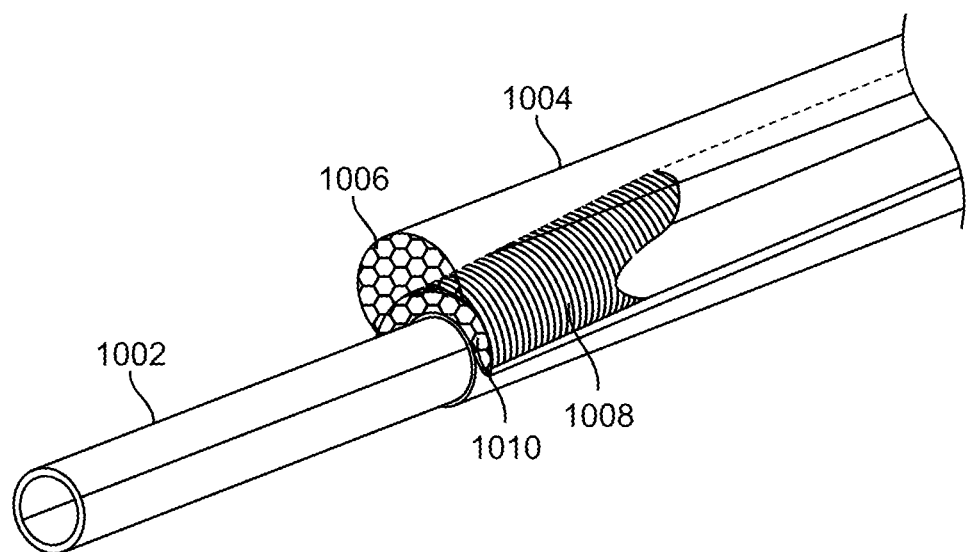
FIG. 10 illustrates a typical illumination element and a tapered tip illumination element disposed over a suction tube.

FIG. 10 illustrates a comparison between a typical illuminated suction instrument and one with a tapered multiplane tip such as previously discussed in FIG. 9. The suction tube 1002 has a typical illumination element such as a waveguide 1004 disposed thereover and has lenslets 1006 on the distal tip of the waveguide. This view is transposed over the tapered tip waveguide having tapers into multiple planes 1008 and lenslets 1010 on the distal tip. It is clear that the improved waveguide has greater surface area and lower profile than the typical waveguide. Therefore, the improved waveguide will have lower energy density and control heat more effectively, and will not obstruct the surgical field as much as the typical illumination element or waveguide. Optical cladding may be disposed between the waveguide and the suction tube in order to prevent light loss from the waveguide. The index of refraction of the optical cladding is preferably in the range from 1 to 1.5. For example, cladding may be a layer of air over the waveguide (index of refraction 1), or various other polymers such as FEP heat shrink (fluorinated ethylene propylene) may be used. Other cladding materials may also be used. The thickness of the cladding is dependent on the material. For example, for some cladding, a cladding thickness of about 5 μm will result in only about 1% light loss, while thinner cladding coatings of 100 nm can result in up to 90% loss. The embodiment in FIG. 10 illustrates a suction tube combined with an illumination element such as an optical waveguide, however one of skill in the art will appreciate that the surgical instrument may be any other surgical instrument including a retractor blade, or other instruments described elsewhere in this specification. Cladding may be used in any of the embodiments disclosed in this specification.

In alternative embodiments, the illumination element may be a waveguide that may be a stand-alone device without coupling the waveguide to a surgical instrument. Thus, the waveguide may be used solely for illuminating the surgical field, or other work space. In still other embodiments, the illuminated suction device illustrated in FIGS. 9 and 10 may have a removable suction tube, thus the device may be used solely to illuminate, or the device may be used with the suction tube as an illuminated suction tube. Various diameters of suction tube may be provided in order to allow different fringe size suction. In still other embodiments, the illumination element may be coupled to any number of other surgical instruments including but not limited to those disclosed in this specification.

Figure 11A:
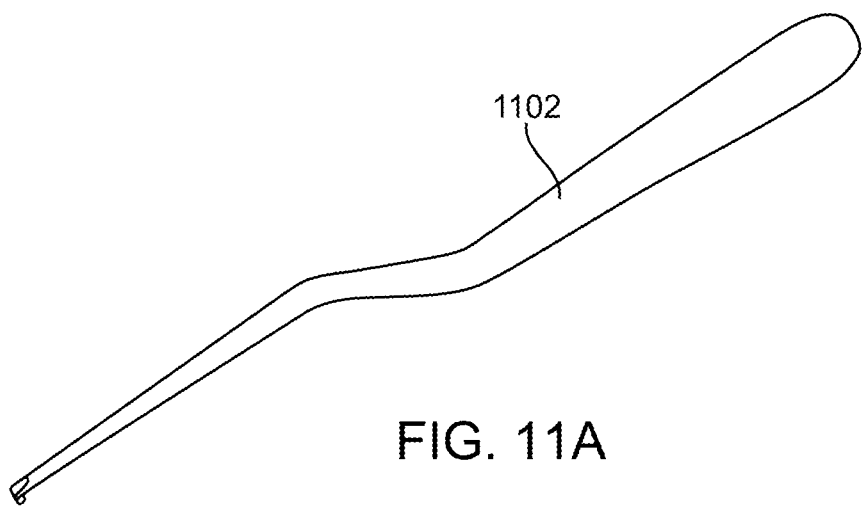
FIGS. 11A-11B illustrate other surgical instruments and tips.
Figure 11B:
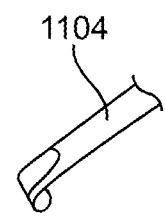
Figure 12:
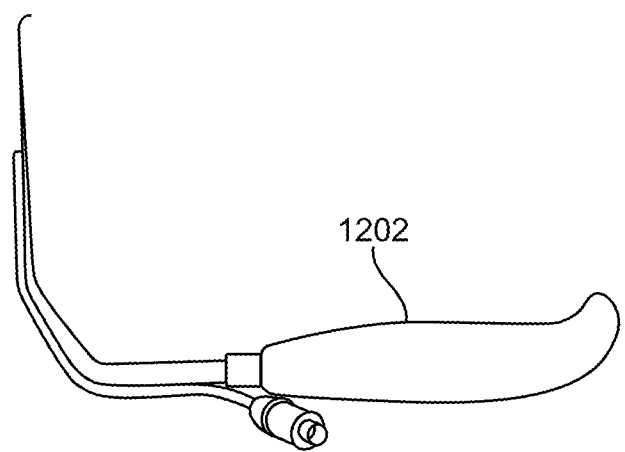
FIG. 12 illustrates still other surgical instruments and tips.

As previously discussed above, the optical waveguide may be used alone, or may be coupled to any surgical instrument to illuminate the surgical field during use of the instrument. Retractor blades and suction tubes are included in the preferred embodiments. Other surgical instruments which may be coupled to an illumination element such as an optical waveguide include but are not limited to such as probes, sensors, imaging elements such as video or other cameras, electrosurgical instruments, navigation instruments, neuro-monitoring instruments, etc. Other surgical instruments include nerve root retractors 1102 as seen in FIGS. 11A-11B having removable tips 1104, or coupled to a nerve root retractor coupled to a handle 1202 in FIG. 12 which clearly shows the profile issues as well as thermal hazard created because all of the light is extracted from the small tip.

Figure 13A:
FIGS. 13A-13D illustrate various embodiments of a surgical instrument with various tips.
Figure 13B:
Figure 13C:
Figure 13D:
Figure 14A:
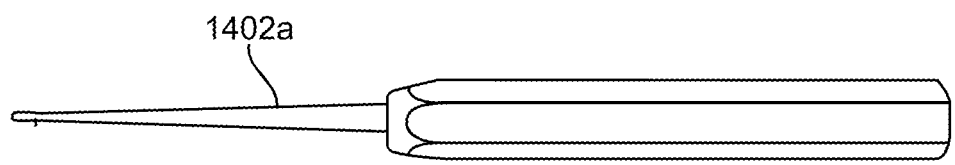
FIGS. 14A-14C illustrate other embodiments of a surgical instrument with various tips.
Figure 14B:
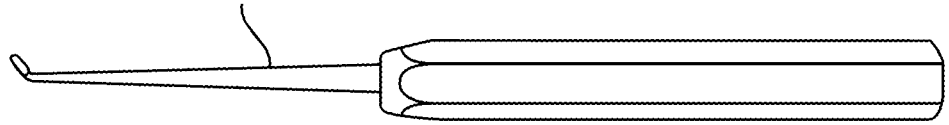
Figure 14C:
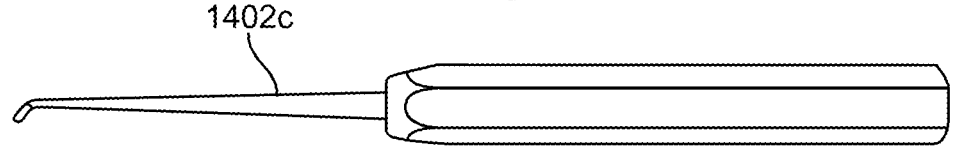

FIGS. 13A-13D illustrate other instruments that may be used with an illumination element like the optical waveguides described herein, such as ball tip probes having an upwardly bending tip 1302a in FIG. 13A, a rightwardly bending tip 1302b in FIG. 13B, a straight tip 1302c in FIG. 13C, and leftward bending tip 1302d in FIG. 13D. Also curettes seen in FIGS. 14A-14C may also be used with any of the illumination elements or optical waveguides described herein. FIG. 14A illustrates a straight tipped 1402a curette, FIG. 14B illustrates an angled tip 1402b curette, and FIG. 14C illustrates a reversed angle tip 1402 curette. In any of these surgical instruments, the illumination element or optical waveguide may be coupled to the entire surgical instrument, or simply the working end or tip of the surgical instrument may be coupled to the illumination element or optical waveguide.

Figure 19A:
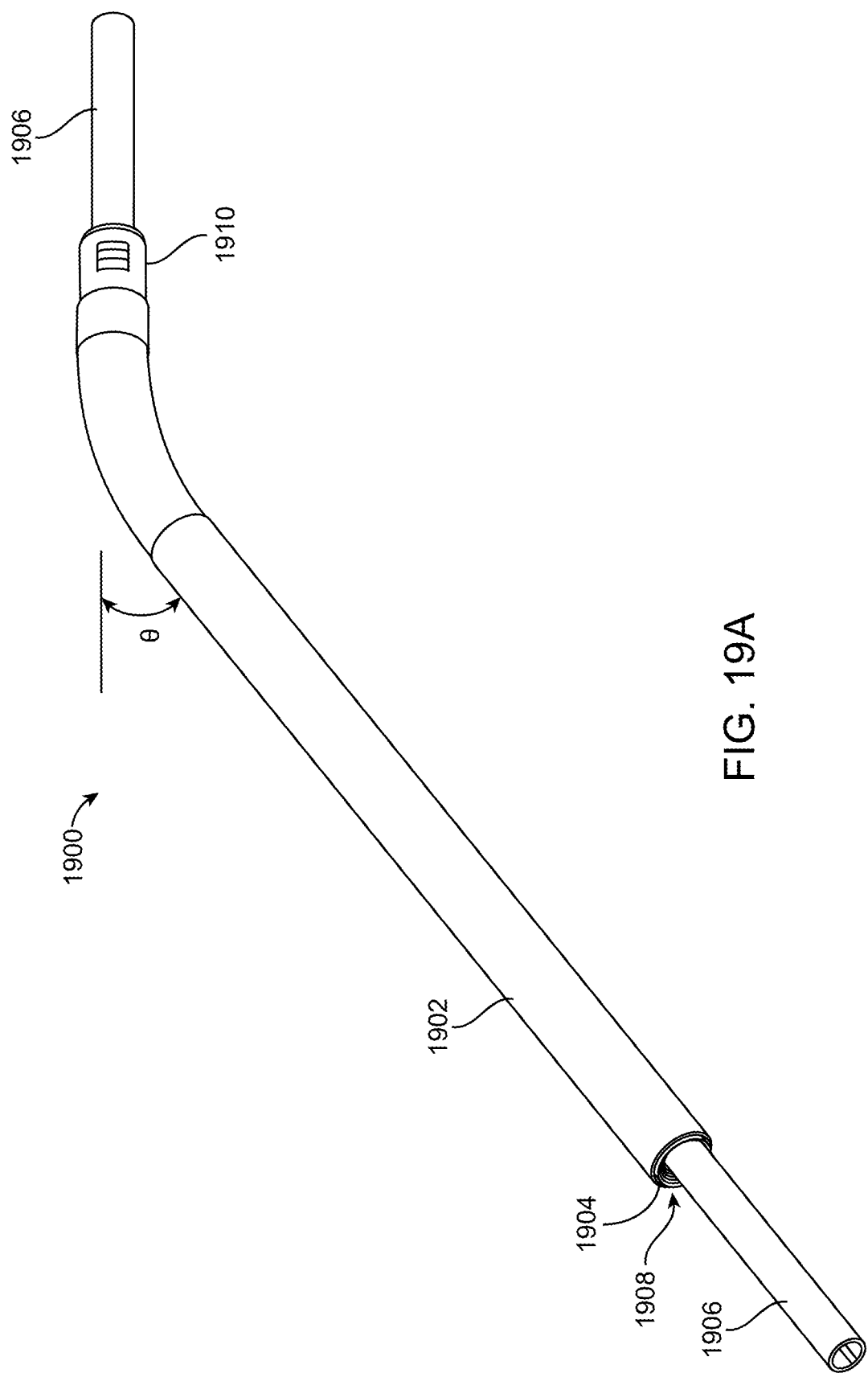
FIGS. 19A-19C illustrate perspective views and a partial cross-section of another exemplary embodiment of an illuminated instrument.
Figure 19B:
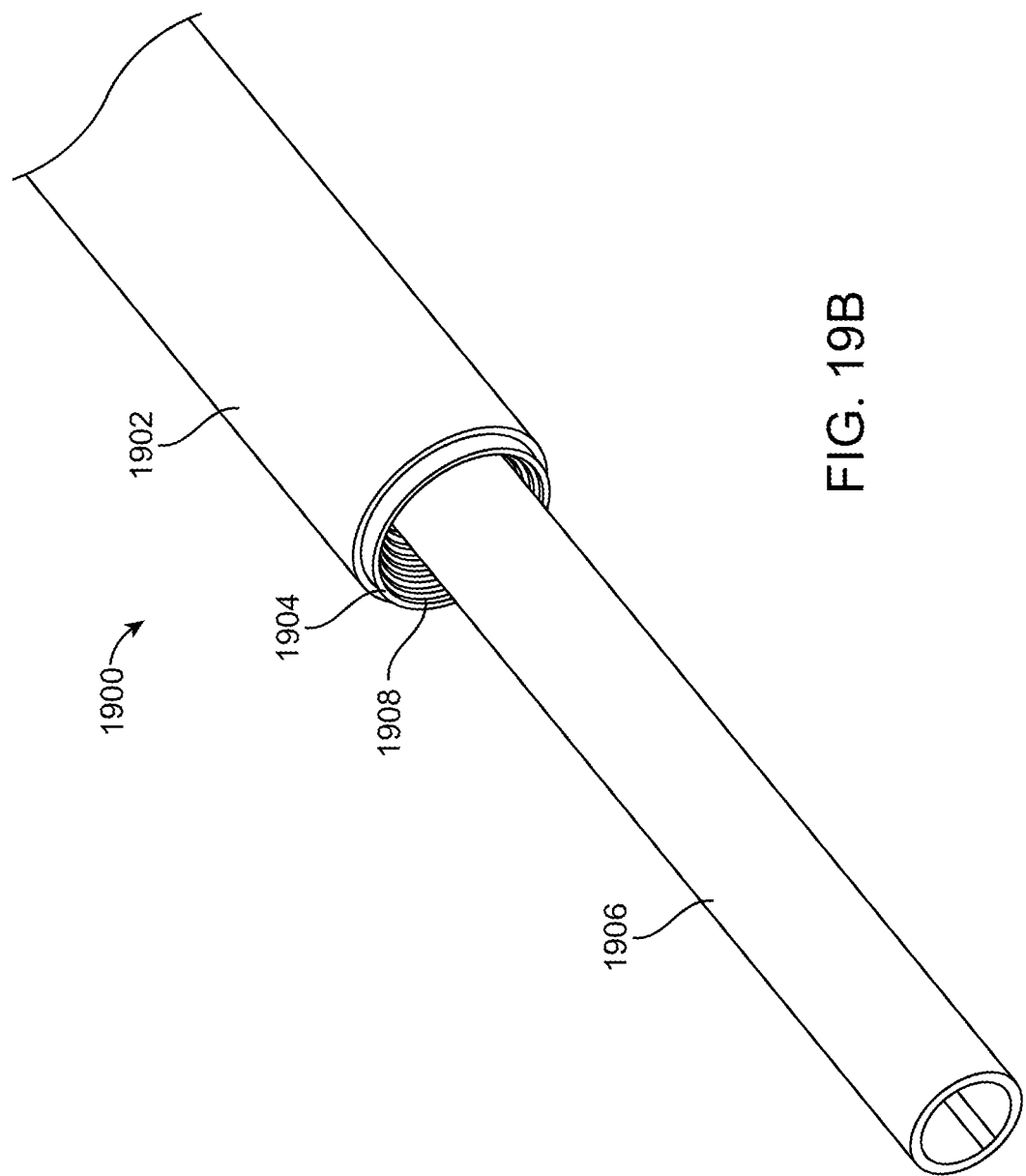
Figure 19C:
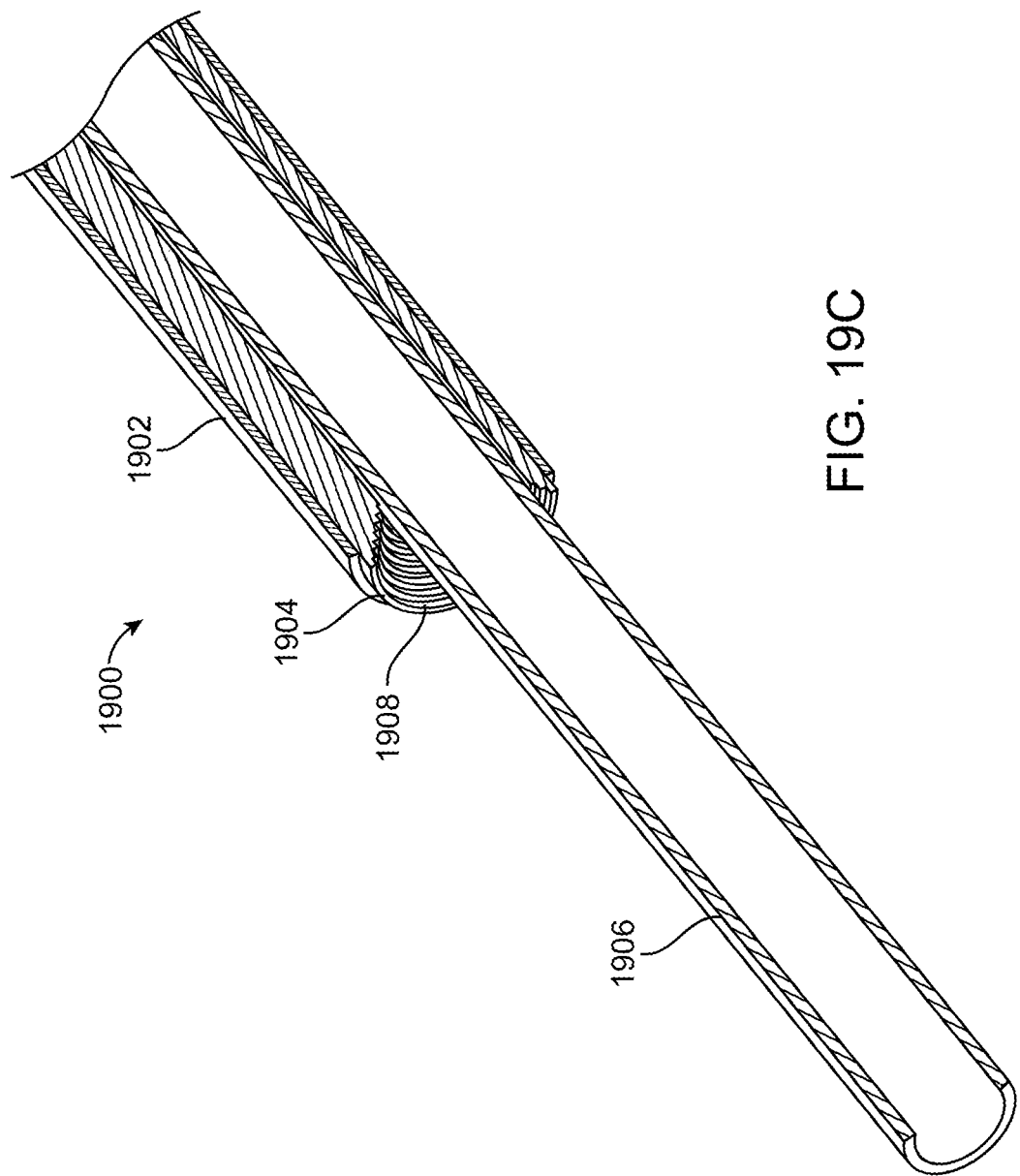

FIGS. 19A-19C illustrate still another exemplary embodiment of an illuminated instrument. In FIG. 19A an illuminated surgical instrument 1900 is an illuminated suction device having a suction tube 1906, an illumination element 1904, and outer cladding 1902. The suction tube 1906 may be any of the suction tubes disclosed herein, and preferably is a metallic or polymeric cylindrical tube with a lumen extending from a proximal end of the suction tube to the distal end of the suction tube. The distal portion of the suction tube is preferably an elongate and linear section, and similarly the proximal portion of the suction tube is also an elongate linear section. A curved or angled region couples the elongate proximal and distal sections such that the distal section forms an angle theta therebetween. The angle theta when measured between the plane in which the proximal portion of the suction tube lies and relative to an upper surface of the plane in which the distal portion of the suction tube lies is preferably an acute angle, but may be any angle based on the anatomy being treated. The proximal end of the suction tube may include an adapter (not shown) such as a barbed fitting or other fluid adapter that allows the proximal end of the suction tube to be fluidly coupled with a source of vacuum. Preferably one end of a flexible polymer suction tube is coupled to the proximal end of the suction tube (not shown) and the opposite end of the flexible polymer suction tube is fluidly coupled to the vacuum source. An engagement element 1910 such as a snap fit, quick release, or other mechanism may be disposed on the proximal portion of the suction tube or the illumination element 1904 so that the suction tube and illumination element assembly may be fixedly or releasably coupled with a handle (not shown).

An illumination element 1904 is disposed over the suction tube 1906. Preferably, the illumination element 1904 is concentric with the suction tube 1906, although this is not required and the illumination element may also be non-concentric (or offset) from the suction tube. The illumination element may take the form of any of the previous illumination elements but in preferred embodiments is a non-fiber optic optical waveguide. The waveguide may be fabricated by injection molding of a polymer thereby forming a homogenous, single piece illumination element. Preferred polymers include those disclosed in this specification, including cyclo olefin polymer (COP), cyclo olefin copolymer (COC), polycarbonates, acrylics, malleable and flexible silicones, as well as other optical materials known in the art. The distal portion of the illumination element is preferably offset from the distal end of the suction tube such that the suction tube contacts tissue or fluid in the surgical field without the distal portion of the illumination element contacting the tissue or fluid. Additionally, the distal portion of the illumination element is preferably an open bore 1908 that extends partially inward into the illumination element. In preferred embodiments, the open bore 1908 is cone shaped 1904 with the larger diameter of the cone closest to the distal end of the illumination element, and the apex of the cone proximally oriented. The cone shape increases the light extraction surface area as previously discussed, thereby facilitating control of heat. Also, since the light extraction surfaces are internally positioned, they are protected from damage caused by adjacent surgical instruments, as well as helping to minimize light loss caused by contact with tissue, blood or other materials, as will be discussed further below. The proximal portion of the illumination element may include a coupling element such as a standard optical coupling element (e.g. ACMI coupling) to optically coupling the illumination element with a light source, such as with a fiber optic cable.

The proximal portion of the suction tube 1906 may remain free of the illumination element. A cladding 1902 may then be disposed over the outer surface of the illumination element. The cladding is selected to have desired optical properties, such as a low index of refraction to help minimize light loss from the illumination element. Exemplary claddings include fluorinate ethylene propylene (FEP) polymer. Other coatings or claddings may be used to minimize light loss from the illumination element. The cladding preferably extends along the entire outer surface of the illumination element. An inner cladding may be disposed between the inner surface of the illumination element and an outer surface of the suction tube to prevent light loss where the two contact one another. An air gap may serve as the cladding to prevent contact between the suction tube and the illumination element. Other coatings or cladding may also be used to provide desired optical or protective properties to the illumination element or adjacent instrument. In some embodiments, a coating or cladding may be selectively applied to either the illumination element or the adjacent instrument so that desired optical or protective properties are selectively disposed on either component. The selective coating or cladding may be applied by masking various regions or by using any other technique known in the art may be used to apply the selective coating or cladding to the desired locations. Thus, the illumination element or the instrument may have a continuous or discontinuous coating or cladding disposed thereon.

FIG. 19B highlights the conical bore 1904 which also has surface features on the inner surface of the conical bore 1904 for extracting and controlling the light that passes through the surface features. The surface features may include lenses, prisms, or any other desired shapes to provide the desired optical properties of the illumination element. Preferably, a plurality of stair steps is formed into the conical bore, each stair step having a riser surface and a step surface. The riser surface preferably is angled to maintain light in the illumination element by total internal reflection, and the step surface is preferably angled to extract light from the illumination element and shape the light and direct the light to a desired portion of the surgical field. The stair steps preferably are formed at least partially circumferentially around the bore, or the stair steps may be formed all the way around the circumference of the bore. As previously discussed, an angle is formed between the riser and the step surface, and this angle may be varied in order to control the light exiting the illumination element, or the angle may be constant. In preferred embodiments, the angle changes from stair step to stair step along the bore. In other preferred embodiments, the riser surface may be a flat planer horizontal surface and the step surface may be a flat planer vertical surface. Any number of stair steps may be used, but preferably there are 1-10 stair steps, more preferably 3-8 stair steps, and more preferably 5-7 stair steps. The bore does not necessary extend all the way through the illumination element. It may be a blind hole. Additional details about the stair steps have been previously disclosed and may apply to this embodiment as well. Thus, the light controlling structures may be on the outer surface of the illumination element, or on the inner surface, or on both surfaces. Using the conical bore on the inner surface of the illumination element is advantageous because it provides a greater cross-section from which the light may exit, thereby controlling heat as previously described with respect to surface features on the outer surface. Also, the surface features may be adjusted to control divergence of the light. Also, since the surface features are on the inner surface of the illumination element, it is less likely that they will be damaged by adjacent surgical instruments, and they are less likely to be masked or otherwise covered by blood or other fluids or tissues during use, thereby further avoiding unwanted heating. And since the surface from which the light exits is on the inside of the illumination element, there is also less likely contact between tissue in the surgical field and the illumination element, therefore there is less chance of causing thermal damage to the tissue. Any of the features described in this embodiment may be combined with or substituted for features from other embodiments disclosed in this specification. And similarly, any of the features described in other embodiments may be combined with or substituted from features from this embodiment.

Figure 20A:
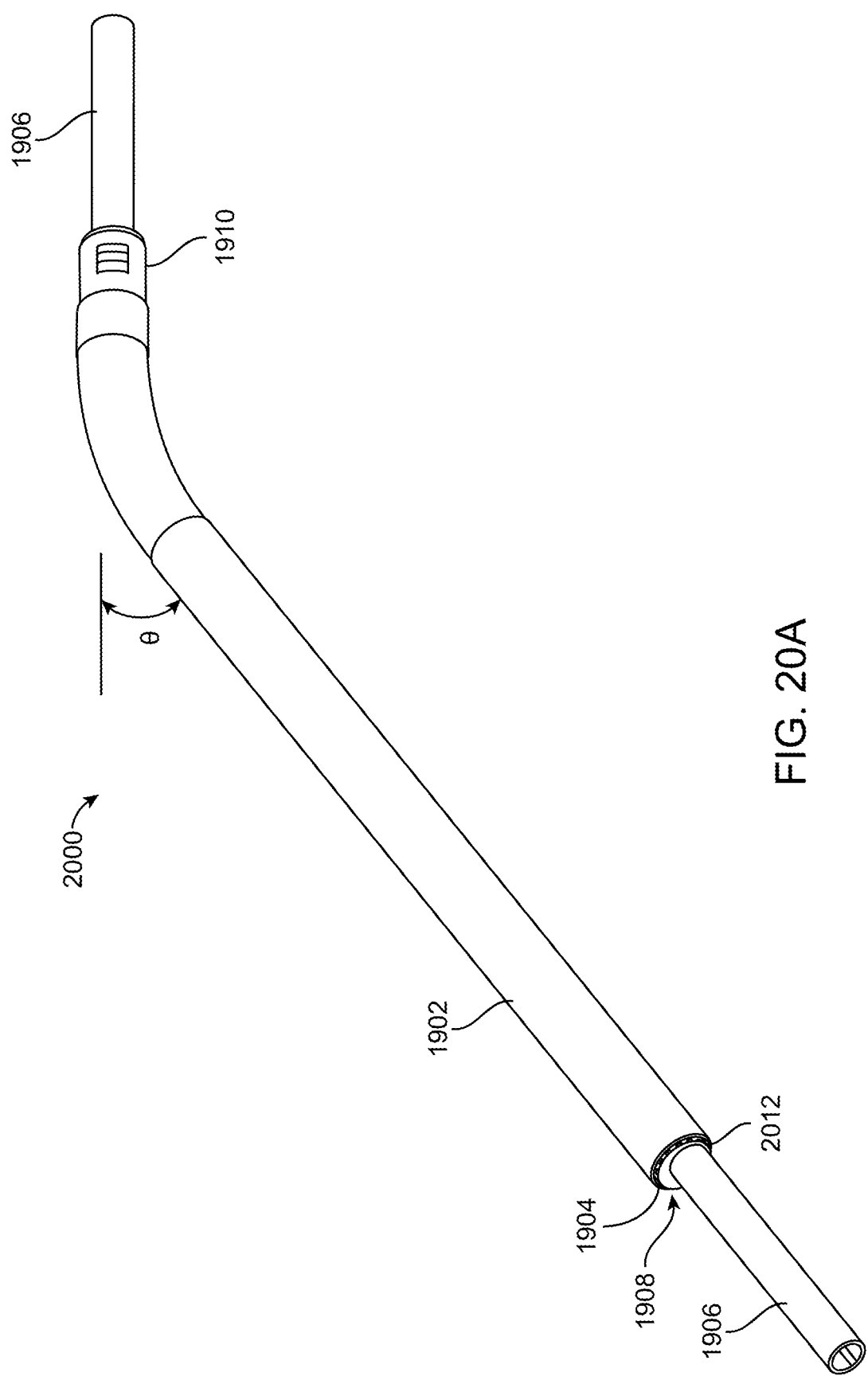
Figure 20B:
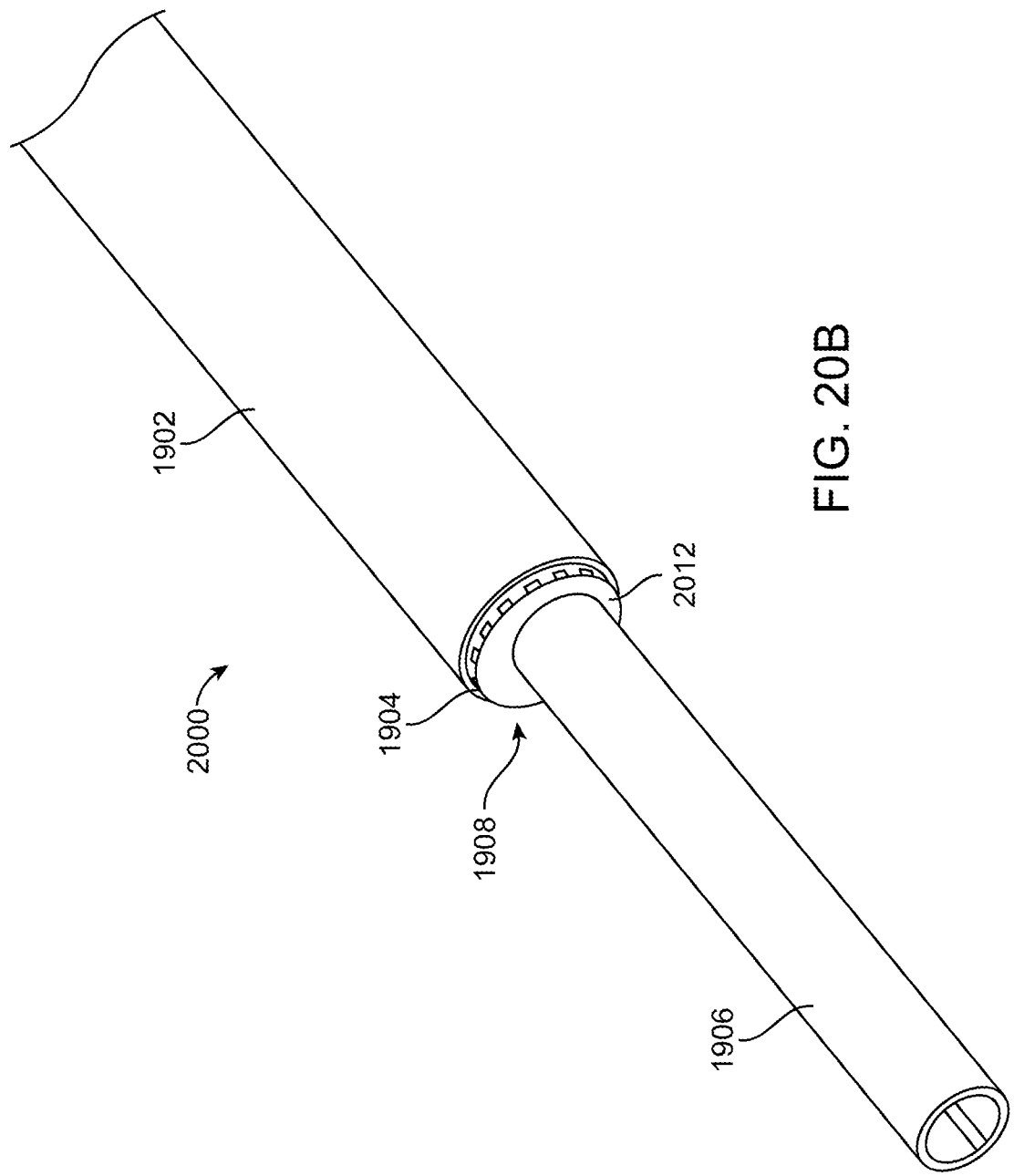

FIGS. 20A-20C illustrate an alternative embodiment of an illuminated instrument 2000 that is substantially similar to the embodiment in FIGS. 19A-19C with the major difference being a cover or protective window 2012 disposed over the distal end of the illumination element 1906 to seal the bore 1904 from tissue, fluid or other debris in the surgical field. The protective window prevents the optical structures on the inner surface of the conical bore from being obstructed by blood or tissue thereby preventing unwanted local heating. Additionally, the protective window may include a filter or polarizer which further allows the light illuminating the surgical field to have desired optical properties. Other aspects of the illuminated surgical instrument 2000 are generally the same as the embodiment in FIGS. 19A-19C. FIG. 20A shows a perspective view of the illuminated instrument 2000, while FIG. 20B highlights the distal portion of the instrument 2000, and FIG. 20C shows a partial cross-section of the instrument 2000 which clearly shows the window and the optical structures. In the embodiments of FIGS. 19A-19C and 20A-20C, the instrument is a suction tube, but one of skill in the art will appreciate that the instrument may be any instrument such as a surgical instrument, a tool, a camera, a sensor, or any other instrument.

Figure 21A:
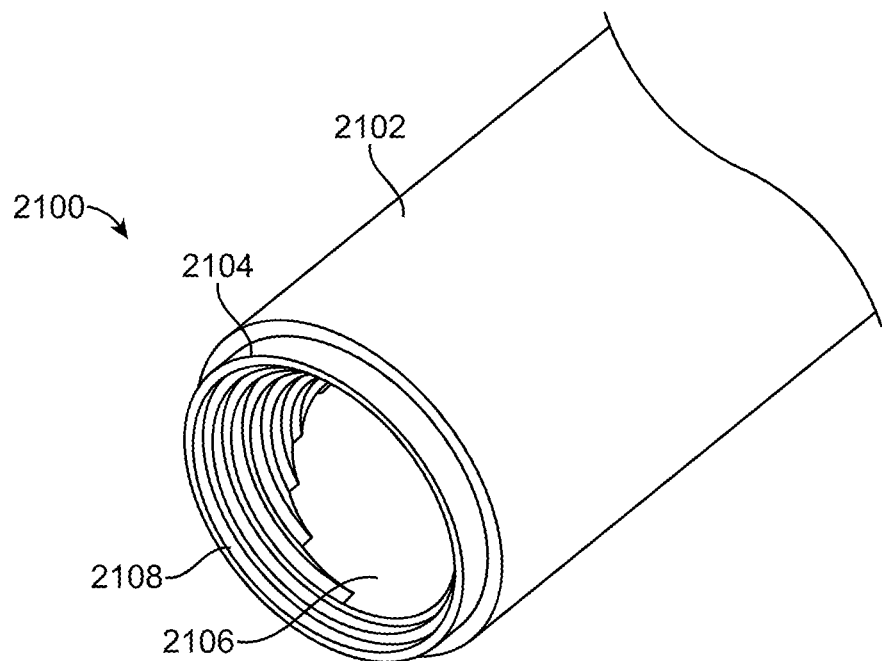
FIGS. 21A-21D illustrate perspective and cross-sectional views of an alternative exemplary embodiment of an illumination element.
Figure 21B:
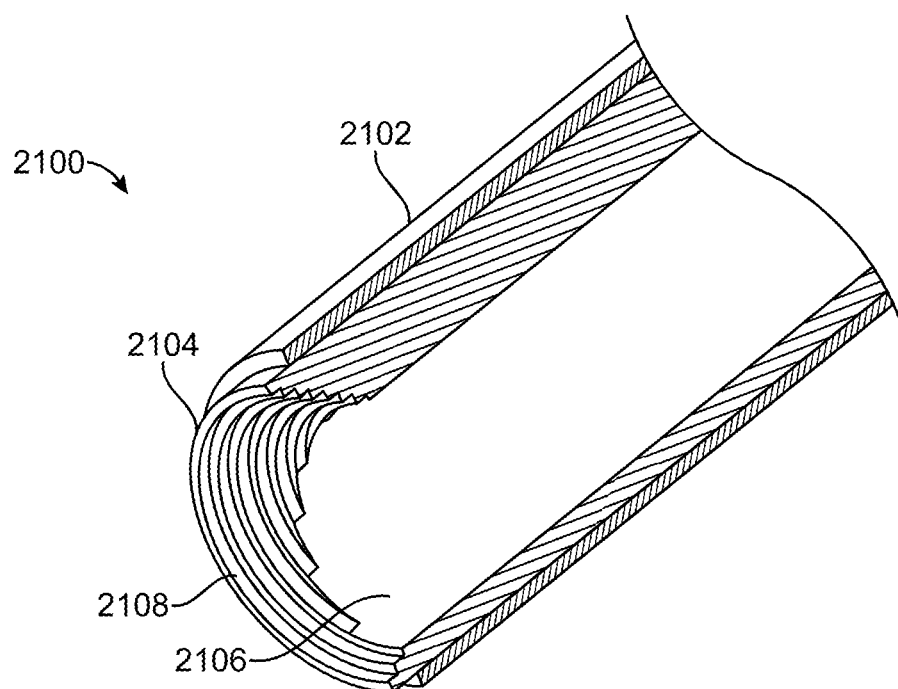
Figure 21C:
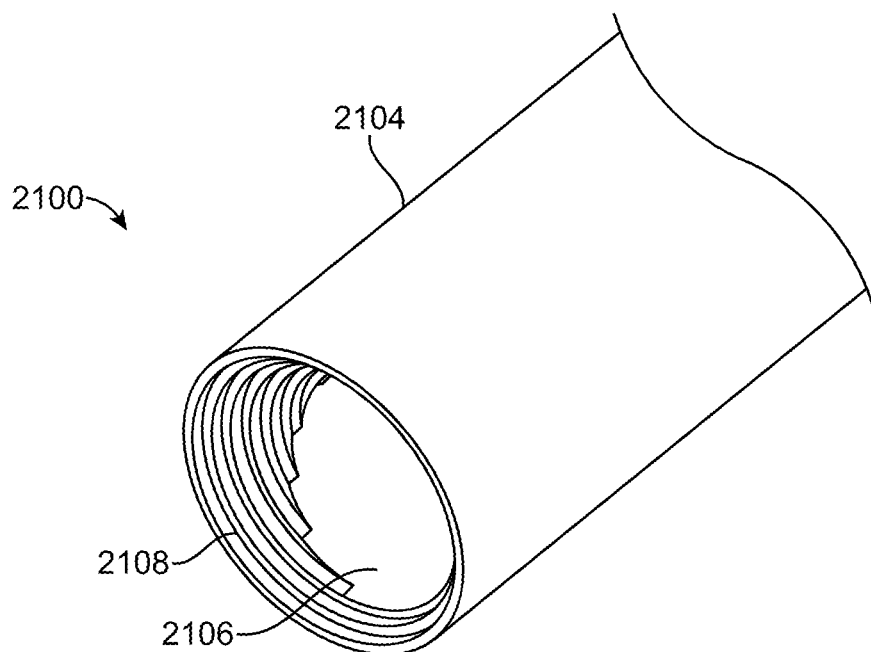
Figure 21D:
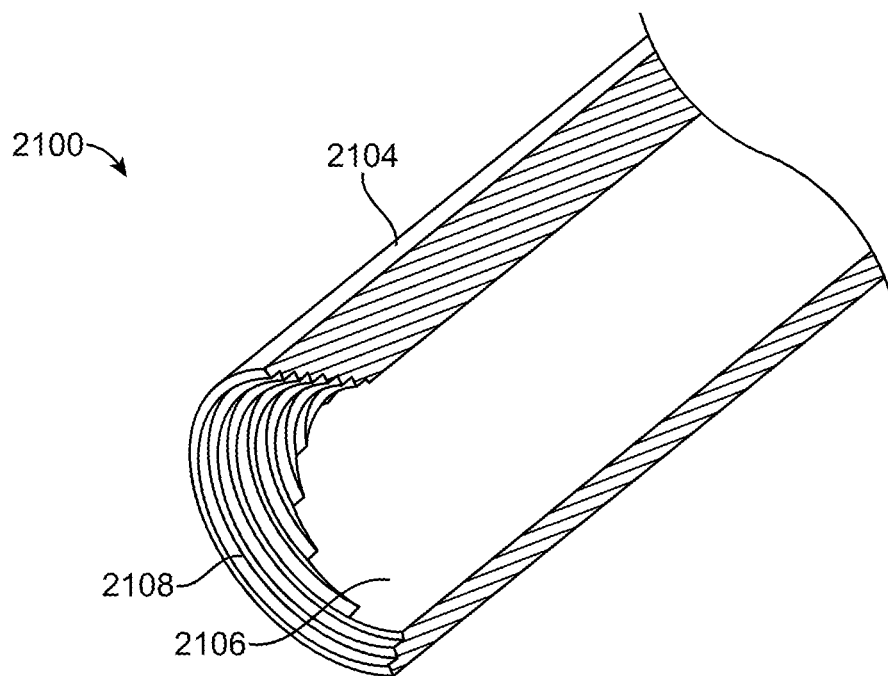

FIGS. 21A-21D illustrate perspective and cross-sectional views of an alternative exemplary embodiment of an illumination element. FIG. 21A illustrates a perspective view of an illumination element 2100 that may be used instead of any of the illumination elements disclosed herein. This exemplary embodiment is similar to the embodiments in FIGS. 19A-19C and 20A-20C with the major difference being the internal conical bore has surface features which extend partially and completely around the circumference of the bore. The illumination element includes cladding 2102 which is generally the same as the cladding previously described above (e.g. cladding 1902) is disposed over an outer surface of illumination element 2104 which includes conical bore 2106. Optical structures 2108 are disposed on the inner surface of conical bore 2106. The structure may be stair steps having a riser surface and a step surface that generally take the same form as those previously described above (e.g. in FIG. 19A-19C or 20A-20C). Yet in this embodiment, some of the stair steps extend around the entire circumference of the bore while other stair steps only extend partially around the circumference of the bore. Those that extend fully around the circumference may be disposed distally, and those that extend partially around the circumference may be more proximally located. The circumferential distance that the stair steps extend around the circumference decreases in the proximal direction. Thus a first stair step which is proximal to a second stair step, extends less around the circumference than the second stair step. The result is that one side of the conical bore has more surface features than an opposite side. This allows light to be extracted preferentially from one side of the illumination element and directed toward one side of the surgical field, unlike in previous embodiments where the stair steps extend entirely around the conical bore and the light is directed uniformly in a beam toward the surgical field. FIG. 21B illustrates a partial cross-section of FIG. 21A highlighting the optical structures on the inner surface of the conical bore. FIG. 21C illustrates the embodiment of FIG. 21A with the cladding 2102 removed, and similarly FIG. 21D is the same view as FIG. 21B but with the cladding 2102 removed.

Figure 22A:
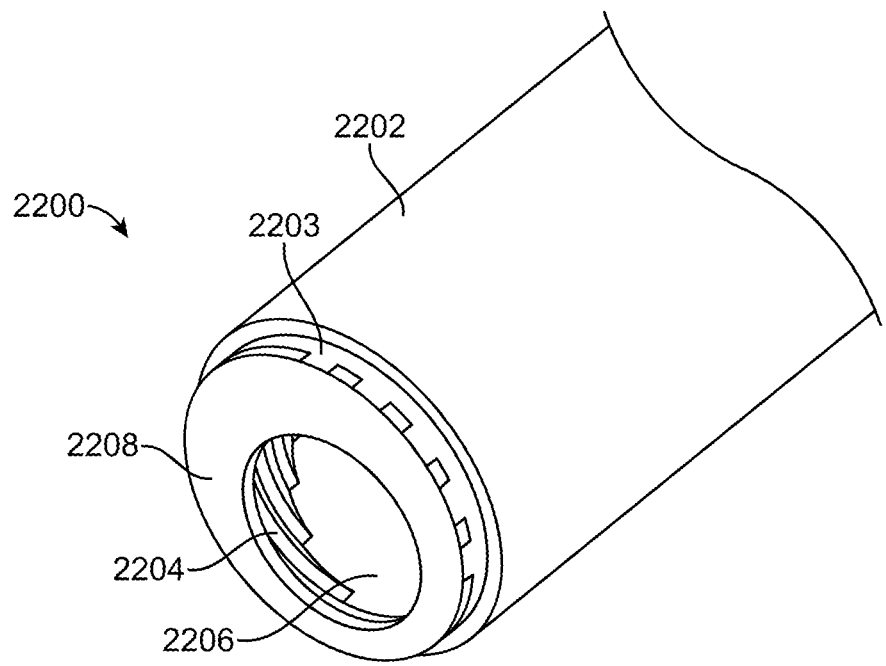
FIGS. 22A-22D illustrate perspective and cross-sectional views of an exemplary embodiment of an illumination element.
Figure 22B:
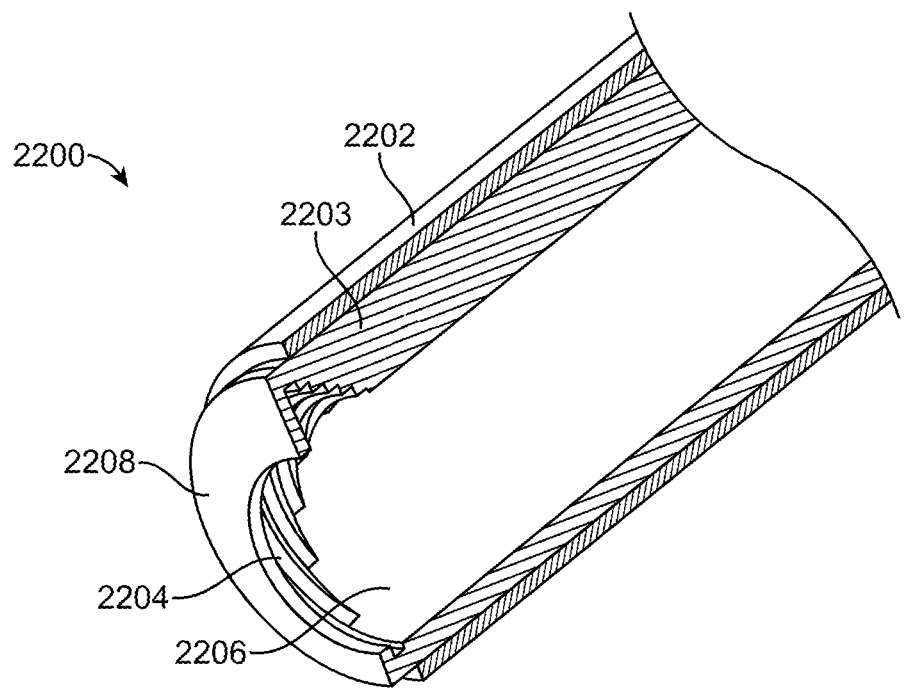
Figure 22C:
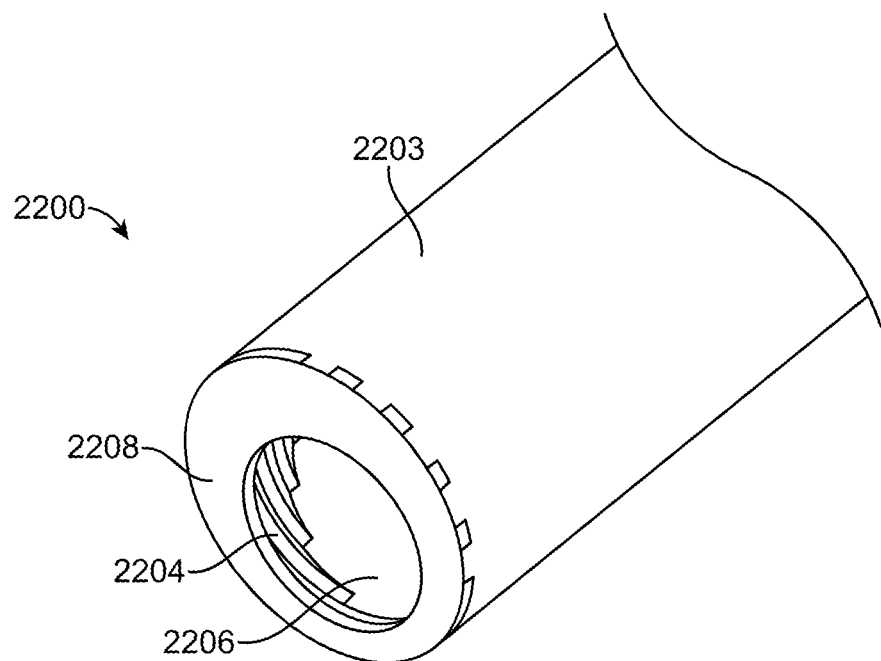
Figure 22D:
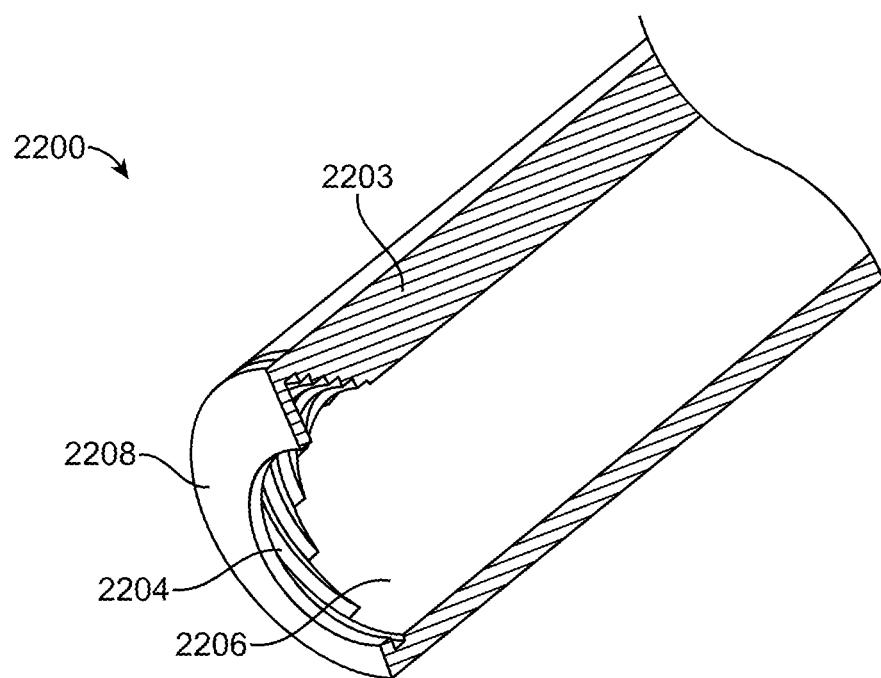

FIGS. 22A-22D illustrate still another exemplary embodiment of an illuminated instrument 2200 without the instrument. It includes illumination element 2203, cladding 2202, conical bore 2206 with optical structure 2204 and cover or window 2208. Aspects of the illumination element 2203, cladding 2202, conical bore 2206 and optical structures 2204 are generally the same as those described previously such as in FIGS. 21A-21D. The major difference being that this embodiment includes cover 2208 to protect the optical structures as previously described above with respect to FIGS. 20A-20C. The cover 2208 includes an aperture in its center and this aperture is sized so that the instrument (e.g. a surgical instrument such as a suction tube) may fit through the aperture. Other aspects of the illuminated instrument are generally the same as previously described. FIG. 22A illustrates a perspective view and FIG. 22B illustrates a cross-section. FIGS. 22C and 22D illustrate similar views of the embodiment but with the cladding removed for convenience.

Figure 33A:
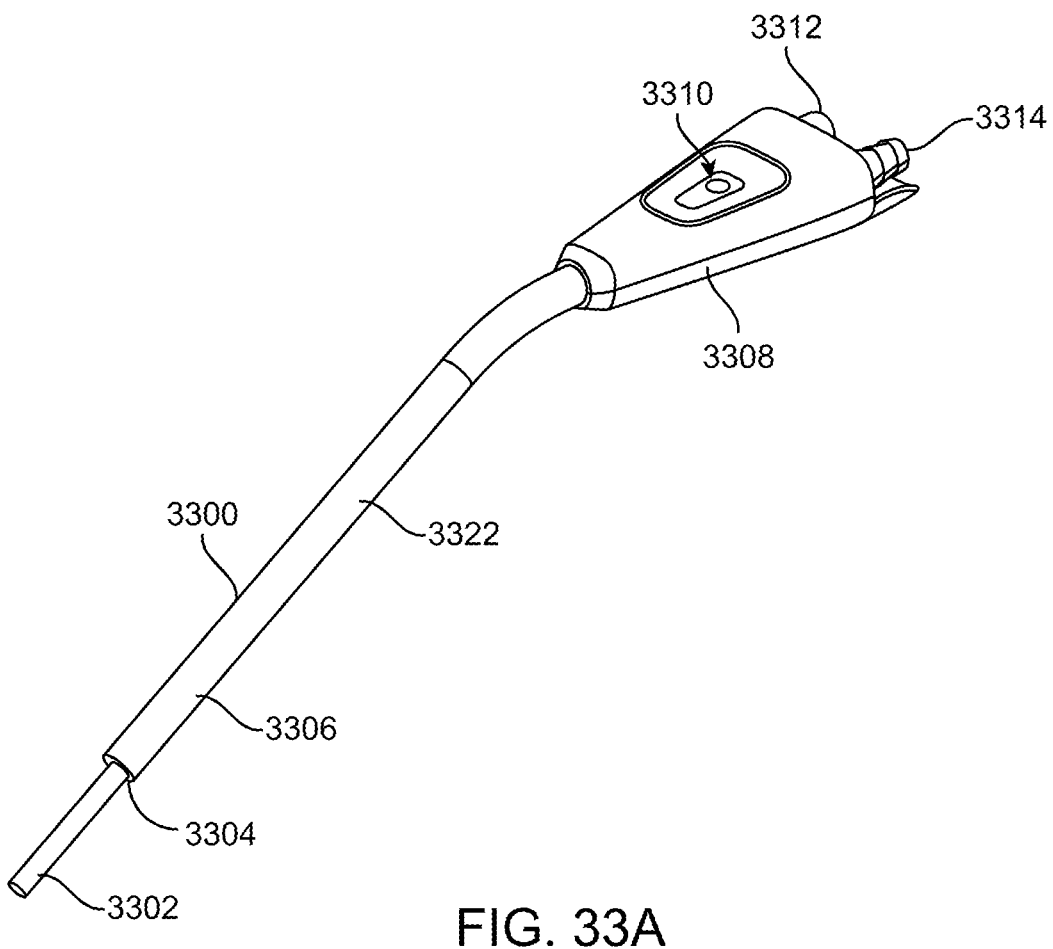
FIGS. 33A-33H show another exemplary embodiment of an illuminated suction device.
Figure 33B:
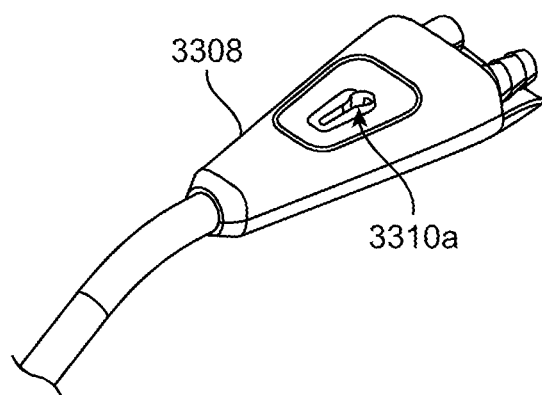

FIGS. 33A-33H show yet another exemplary embodiment of an illuminated instrument, here an illuminated handheld suction device. FIG. 33A shows a perspective view of an illuminated suction device 3300 which includes a handle 3308 at the proximal end of the device and a waveguide 3306 and suction tube 3302 with outer cover 3322 extending distally from the handle 3308. The waveguide 3306 is disposed over the suction tube 3302 and illuminates the surgical field distal to the suction tube. The tip of the waveguide preferably does not extend all the way to the distal end of the suction tube. The distal end 3304 of the waveguide may have any of the surface features described herein. In this embodiment, an inner conical bore extends partially into the waveguide to increase the output surface area, and stair step surface features may be disposed circumferentially along the conical bore. The stair steps may extend partially or completely around the circumference of the conical bore. The handle 3308 is preferably symmetrical so that left-handed or right-handed physician may comfortably use the device. A suction control hole 3310 may be disposed in the handle and is in fluid communication with the suction tube. The hole may be a round hole and the physician or operator may press a finger or thumb over the hole to coarsely adjust suction being applied to the surgical field. FIG. 33B shows an alternative embodiment of a suction control hole 3310a where the hole is either a tapered slot or tear drop shaped and this allows the physician to finely adjust suction by covering all or portion of the suction hole which is fluidly connected to the suction tube. Optionally, an insert may be disposed in the round suction hole to convert it into the tapered slot/tear drop suction hole, or an insert may be disposed in the tapered slot/tear drop suction hole to convert it into a round suction hole. The proximal end of the handle includes an optical connector (e.g. an ACMI connector) and a fluid connector (e.g. a barbed connector). The optical connector allows the waveguide to be optically coupled to a light source and the barbed fitting allows suction tubing to be coupled to the suction tube so that vacuum may be applied. The elongate portion of the suction tube and waveguide may be straight and angled relative to the shorter section of the waveguide and suction tube coupled to the handle.

Figure 33C:
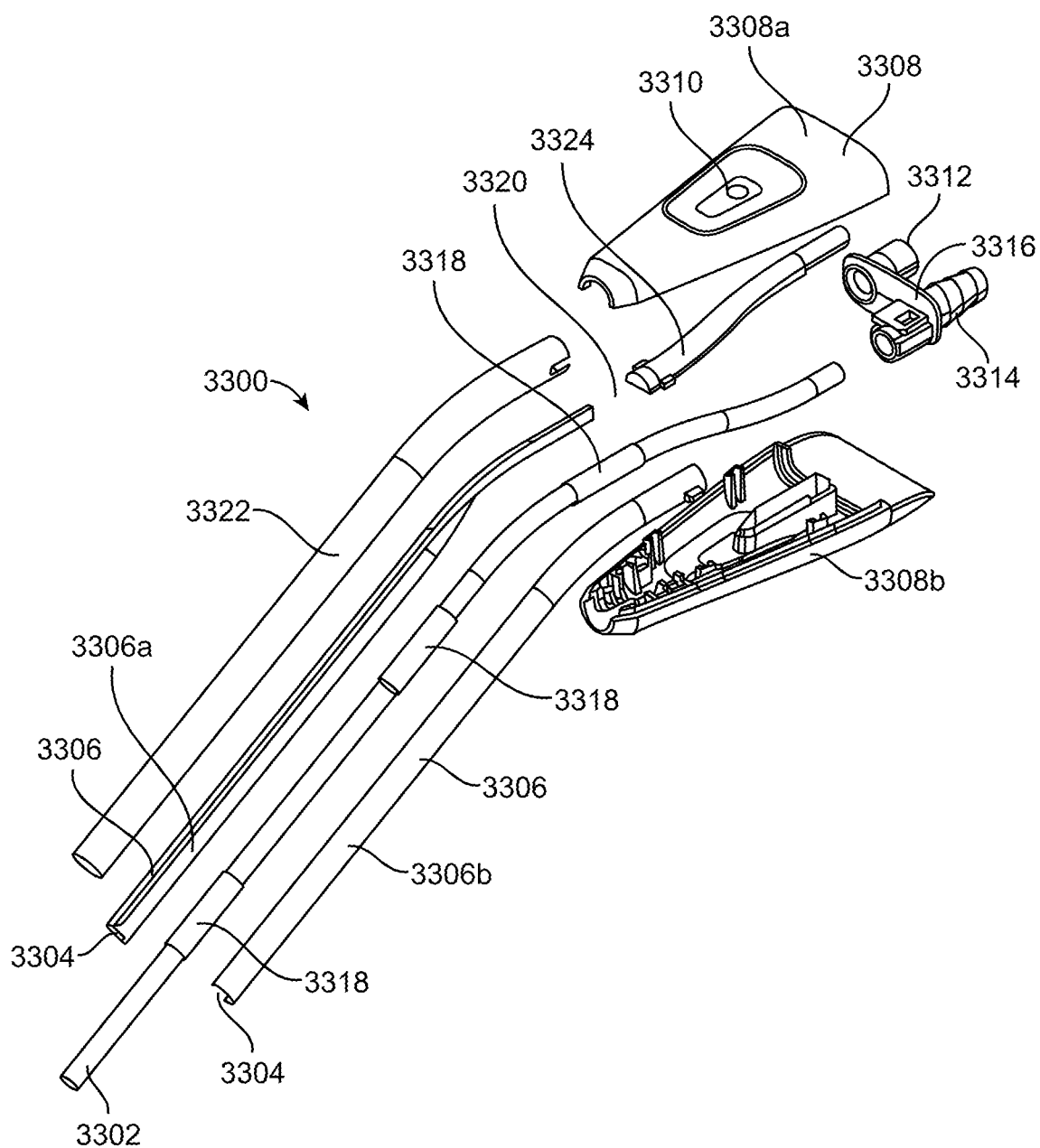

FIG. 33C shows an exploded view of the illuminated suction device 3300 seen in FIG. 33A. The suction tube may formed from any material but is preferably metal. The suction tube may also be used to deliver electrical energy to the target tissue during surgery or it may have discrete electrodes disposed on the suction tube for delivering the electrical energy. One or more spacers 3318 (here three spacers) may be disposed over the suction tube such as distally, proximally and centrally in between the proximal and distal spacers. The spacers prevent adjacent components such as the waveguide from directly contacting the suction tube thereby helping to minimize light loss at the points of contact. An exemplary spacer is a tube of FEP heat shrink material (fluorinated ethylene propylene) preferably having an index of refraction lower than the index of refraction of the waveguide. Preferred embodiments of the waveguide are formed from cyclo olefin polymer or cyclo olefin copolymer, and the waveguide 3306 is molded in two halves 3306a, 3306b that may be clamped together over the suction tube to form a closed tube. An outer cover 3322 may then be disposed over the waveguide halves to secure them to one another. Here, the outer cover is formed from FEP heat shrink which again preferably has an index of refraction lower than the waveguide material in order to minimize light loss from waveguide. The inner conical bore 3304 having stair steps is also formed by joining the two halves of the waveguide together.

The handle 3308 includes a top half 3308a and a bottom half 3308b that may be clamped together and snapped together, welded together or boned together to secure the waveguide and suction tube to the handle. A light input stem 3324 is also optically coupled to the proximal portion of the waveguide 3306. An air gap 3320 or index matching material may be disposed between the two ends in order to efficiently transfer light therebetween. The proximal end of the input stem and the proximal end of the suction tube are coupled to the optical connector 3312 and the barbed fitting 3314 so that light and vacuum may be connected to the device. A plate 3316 holds both the barbed fitting and the optical connector in position and to the handle. This embodiment includes the round coarse adjustment vacuum hold 3310 but this may be substituted with any other vacuum control hole disclosed herein.

Figure 33D:
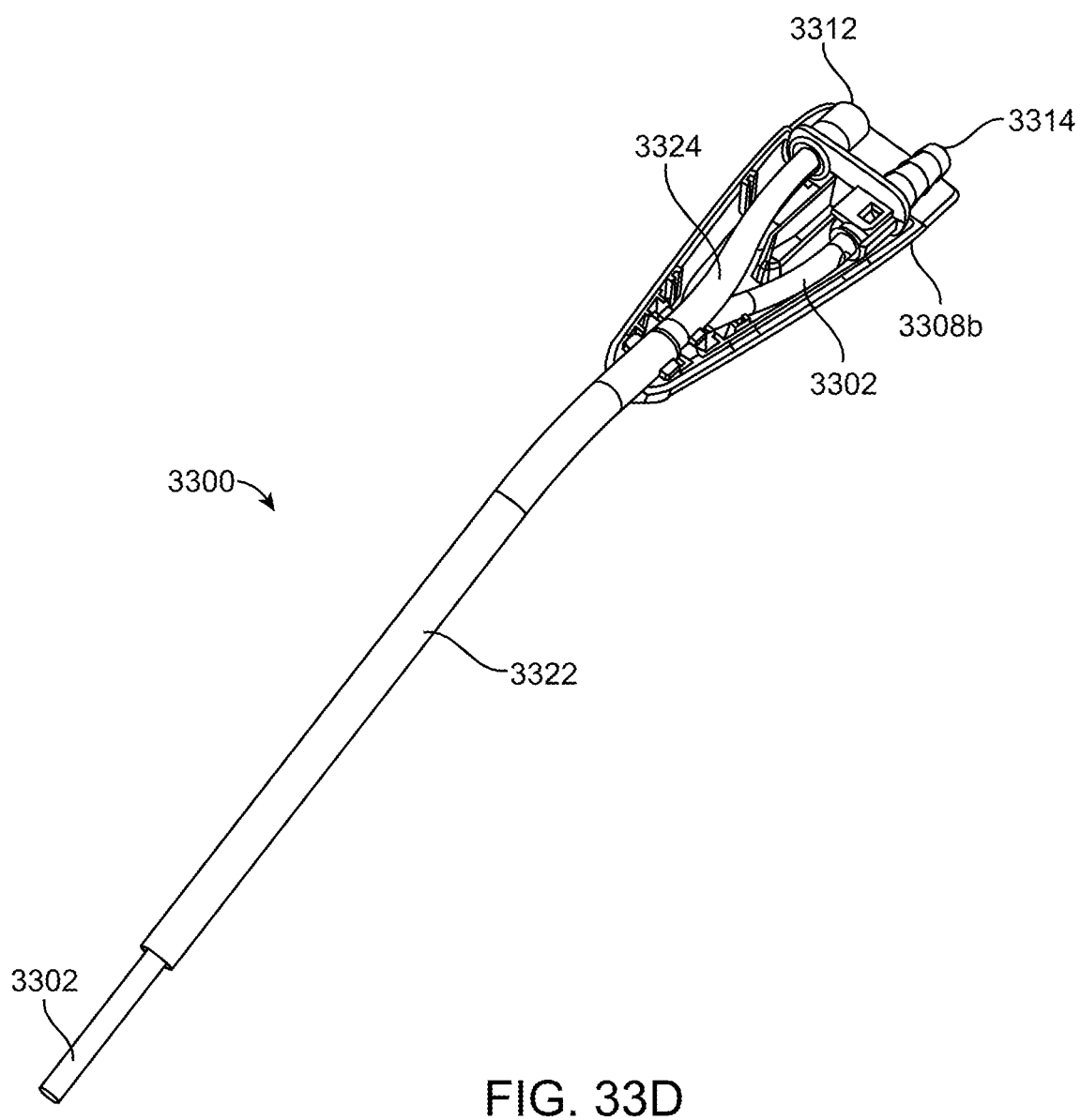

FIG. 33D shows the illuminated suction device 3300 with the top portion of the handle removed. The distal portion of the suction tube may be bendable in order to allow a physician to conform the suction tube to the native anatomy.

Figure 33E:
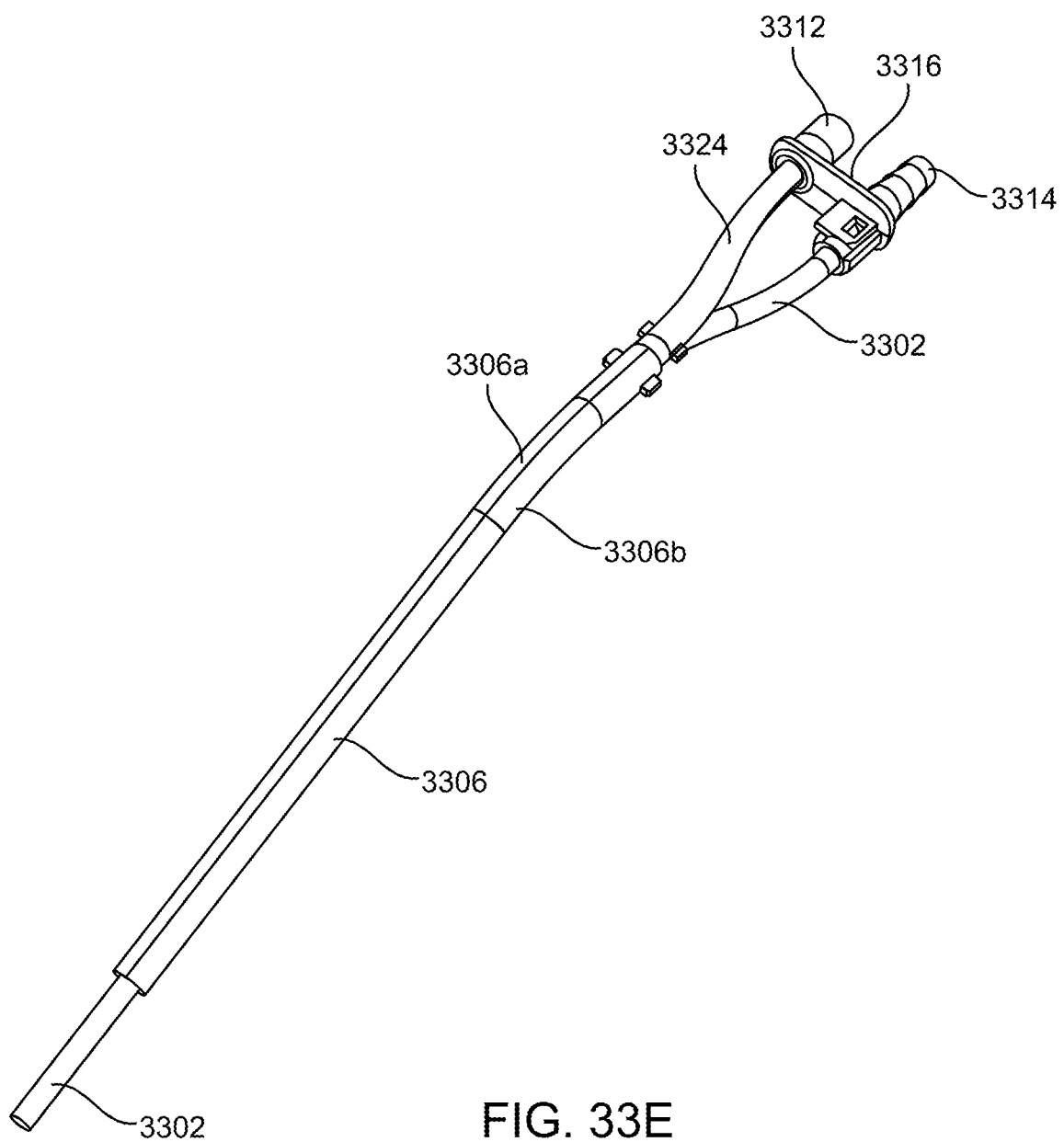
Figure 33F:
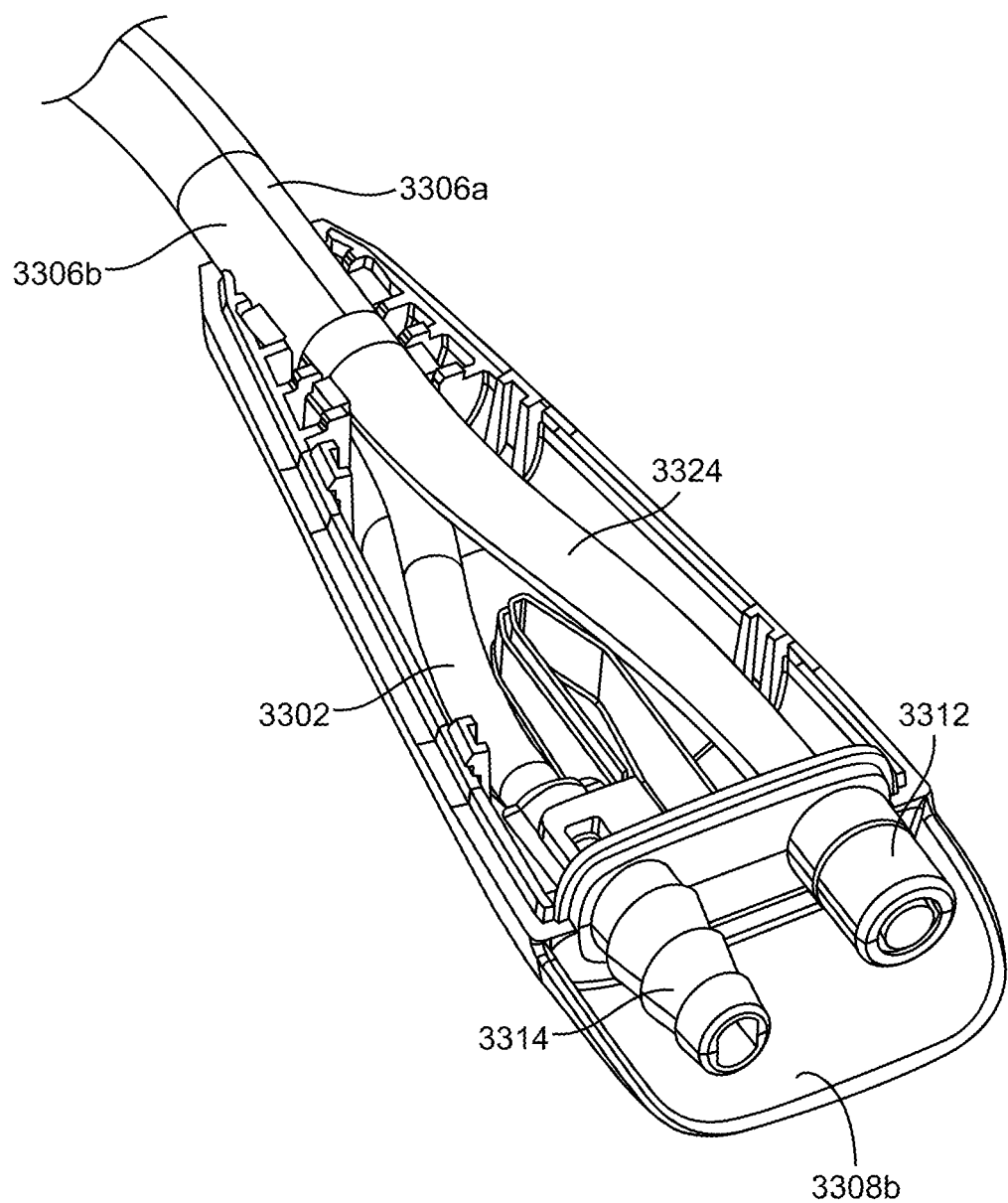

FIG. 33E illustrates the illuminated suction device 3300 with the handle 3308 and the outer cover 3322 removed and highlights the suction tube, the waveguide, input stem and connectors.

FIG. 33E illustrates the proximal portion of the illuminated suction device 3300 with the top handle cover removed. The proximal portion of the suction tube is bent into an S-shaped curve in order to smoothly transition from the elongate straight section of the suction tube to the barbed connector. Similarly, the input stem is also formed into an S-shaped curve in order to join the waveguide to the optical connector. Ribs in the handle provide stiffness and rigidity to the handle and also form recesses or channels for receiving the suction tube or the input stem.

Figure 33G:
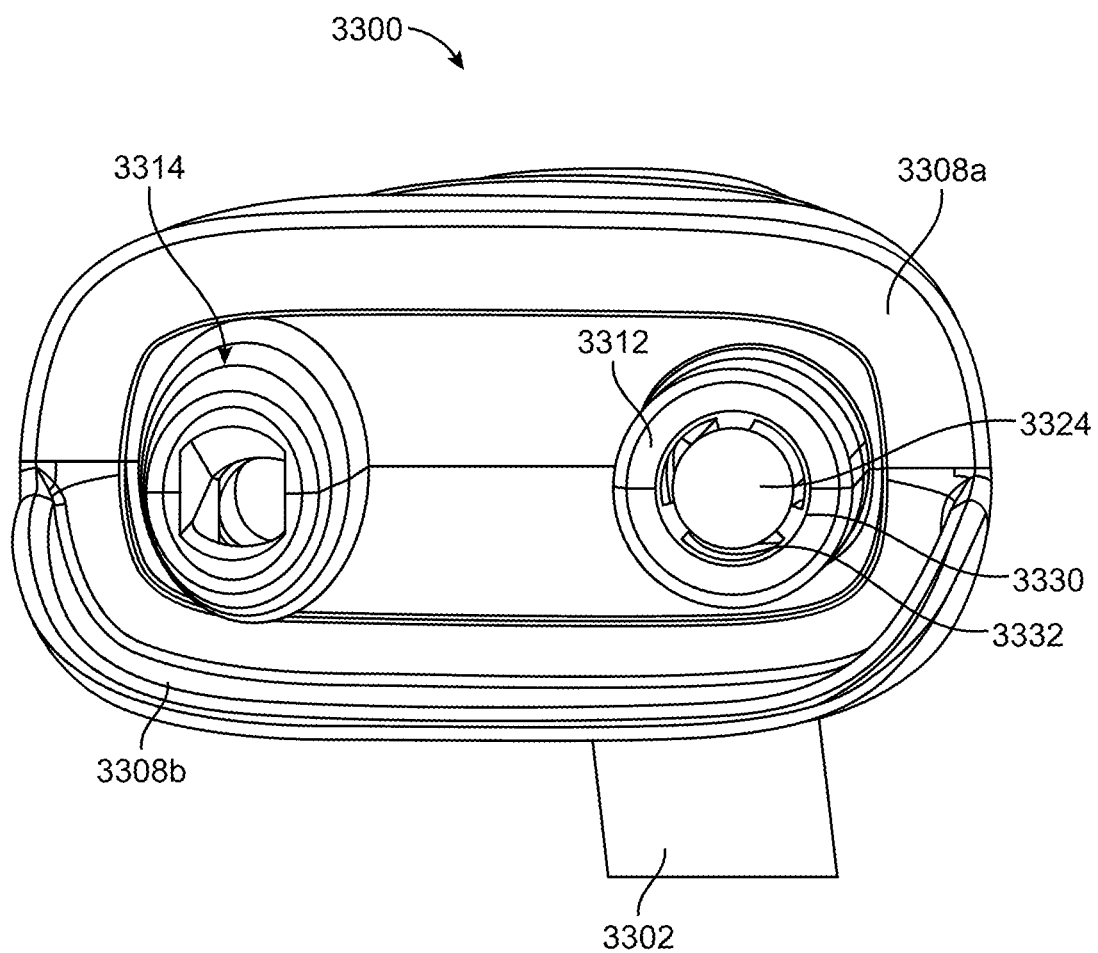

FIG. 33G shows and end view of proximal portion of the illuminated suction device 3300. Ribs 3330 disposed around the circumference of the optical connector 3312 minimize direct contact between the input stem 3324 and the connector 3312. The ribs provide standoffs that form result in an air gap 3332 between the input stem and the connector. The air gap helps minimize light loss from the input stem.

Figure 33H:
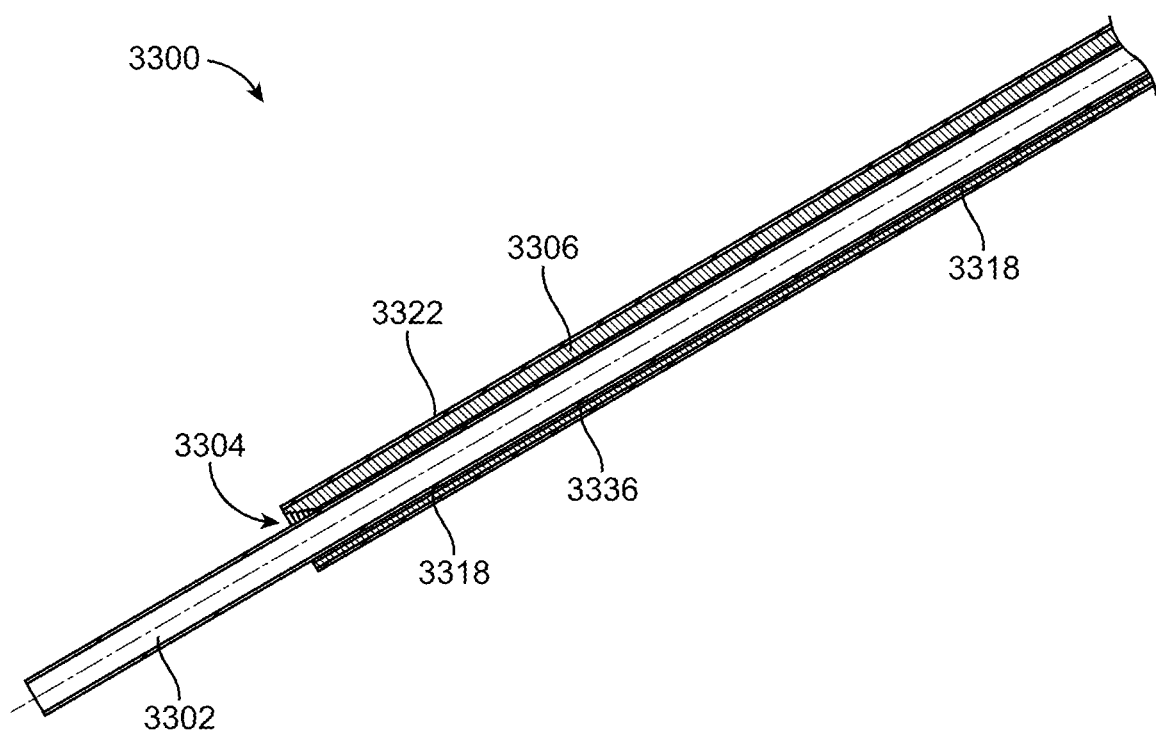

FIG. 33H shows a cross-section of the illuminated suction device 3300 and highlights the air gap 3336 between the waveguide 3306 and the suction tube 3302 that is due to the FEP layers 3318. The FEP and air gap help minimize light loss from the waveguide. Also the tapered conical inner bore with optical surface features is also seen at the distal end of the waveguide. As previously discussed, the tapered bore provides increased surface area which helps control energy density and heat.

In this exemplary embodiment, the illuminated instrument is an illuminated suction device. However, this is not intended to be limiting. The instrument may be any other instrument such as other instruments, tools, or even cameras, sensors, surgical instruments, laparoscopic instruments such as a grasper or clip applier, etc. The suction device or the instrument maybe malleable so that a physician can bend the instrument to conform to the native anatomy. Similarly, the waveguide may also be malleable along a portion, or along the entire length of the waveguide so that it may be bent or formed independently or in conjunction with the suction tube or other instrument to conform to the native anatomy. Preferably white light is delivered by the waveguide, but in other embodiments other wavelengths may be delivered. For example other wavelengths of visible or near infrared light may be delivered by the waveguide, or any other electromagnetic energy may be delivered.

Additional Waveguide Geometries

In addition to the waveguide geometries discussed above, other geometries are contemplated that may be used to deliver light to illuminate a target and that control heat. These waveguides may be used in any of the illuminated systems described herein. Any of these may be injection molded, or alternatively they may be extruded, compression molded, coined, cast, or even machined directly.

Figure 23A:
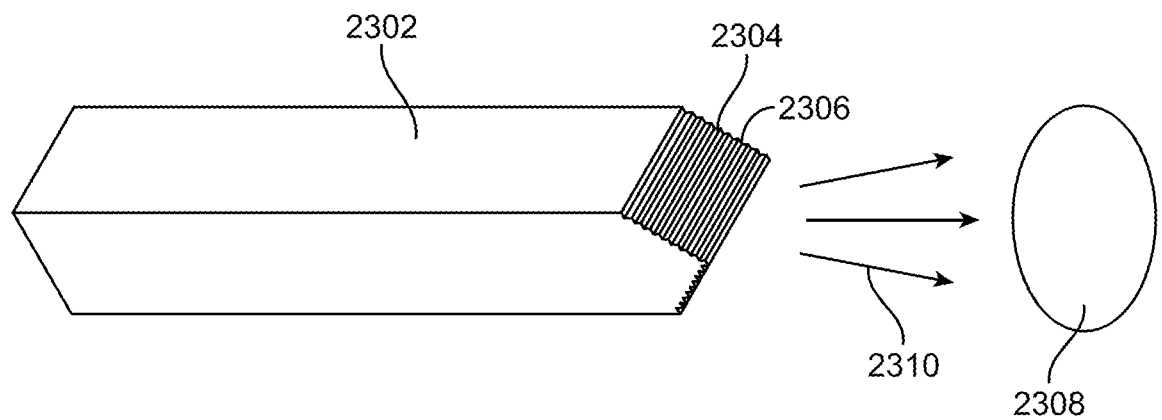
FIG. 23A shows a perspective view of an exemplary waveguide with optical surface features.
Figure 23B:
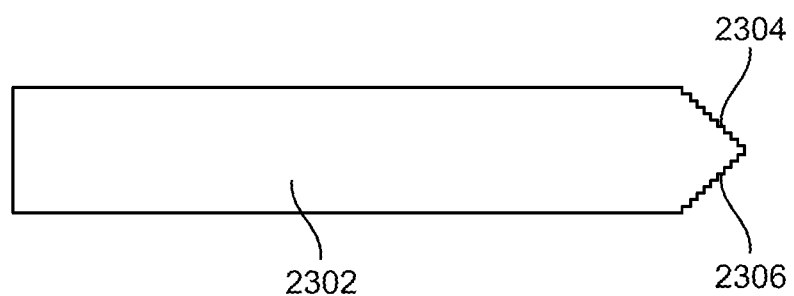
FIG. 23B shows a side view of FIG. 23A.

For example, FIG. 23A shows a perspective view of waveguide 2302 having a square or rectangular cross-section and a wedge-shaped and pointed tip 2304. The upper and lower outer surfaces of the wedge shaped tip 2304 may have surface features 2306 on one or both sides of the wedge shaped tip that extract and control the light to direct it toward a desired target area. The surface features here include a plurality of stair steps such as those previously described above with a riser surface and a step surface that may be the same as those previously described above. The riser and step surfaces may have any dimensions and may have any desired angle in order to preserve total internal reflection and direct the extracted light 2310 to a desired target illumination area, preferably a spot of light 2308. The stair steps may include a plurality of facets, and they may be disposed along a portion of the wedge-shaped tip, or along the entire wedge-shaped tip. FIG. 23B shows a side view of FIG. 23A.

Figure 24:
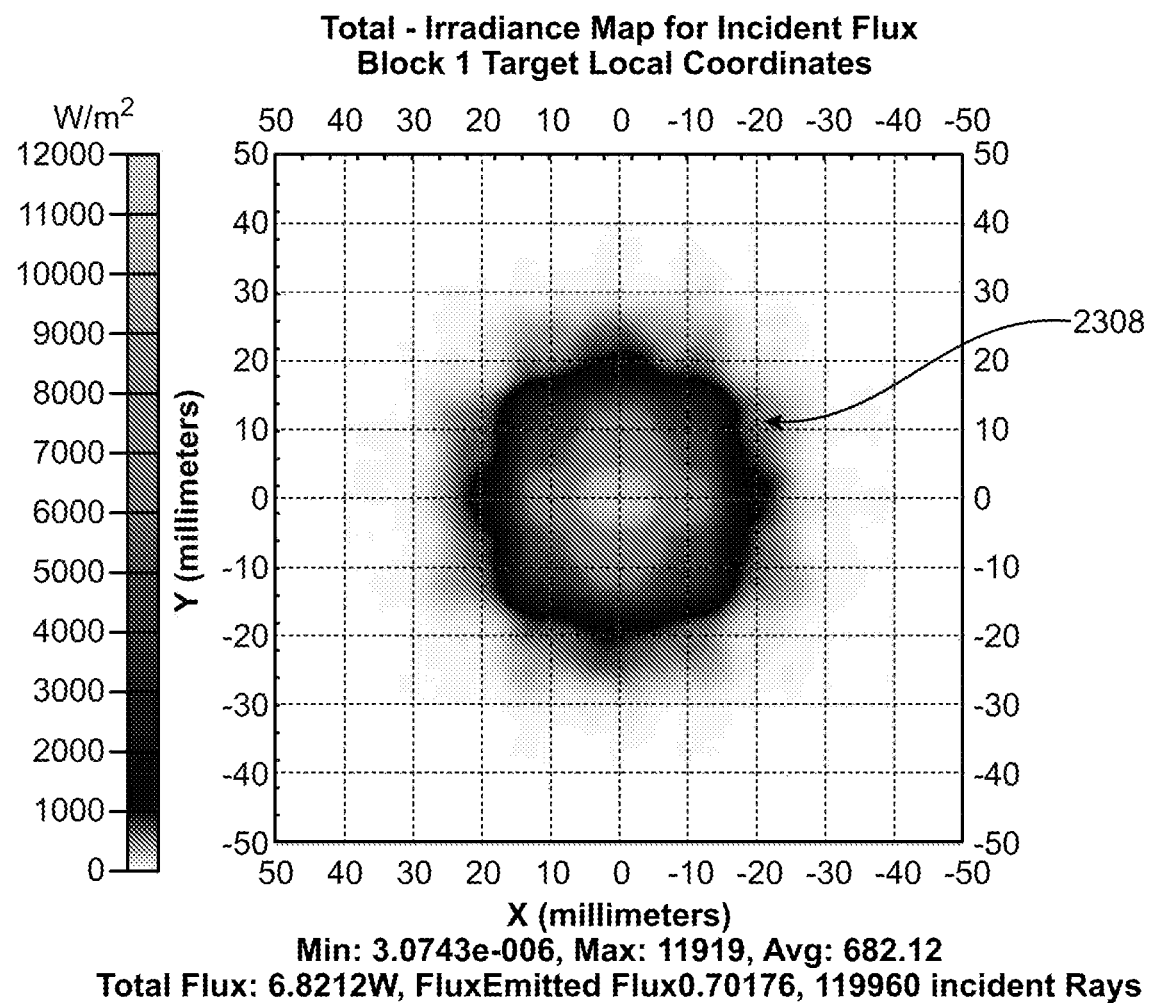
FIG. 24 illustrates an exemplary illumination spot provided by the waveguide in FIGS. 23A-23B.

FIG. 24 shows the preferred spot of light 2308 that is emitted from the waveguide shown in FIGS. 23A-23B. The illumination pattern is rectangular with a bright spot in the middle. The rectangular shape matches the overall shape of the waveguide. Here, the spot is roughly square to correspond with the square cross-sectional shape of the waveguide in FIGS. 23A-23B. If the shape of the waveguide was more aggressively rectangular, the spot size would match. The bright spot in the middle is an image of the original source fiber with flat grooves and vertical walls forming the stair steps. However, in alternative embodiments additional microstructures or other surface features may be disposed on the waveguide such as on the individual grooves or including curvature on the grooves, angling the grooves or by using a separate diffuser or lens array. The angular spread of the pattern in these models is preferably the same as the fiber. In this exemplary embodiment, this includes 0.55 NA, or about +/−33 deg. This can be modified of course. Adding angles, curvature, or other microstructures onto the surfaces of the waveguide can widen the pattern as required. These surfaces can be used to narrow the pattern as well. However this is not necessarily the best solution. Etendue is preferably preserved, and a narrower pattern with the same cross sectional area would result in the leakage of light in the waveguide. This may be seen as scattered light, a loss of efficiency, glare, or all of the above. The concepts discussed in relationship to FIG. 24 may apply to any of the other waveguides discussed herein.

Figure 25A:
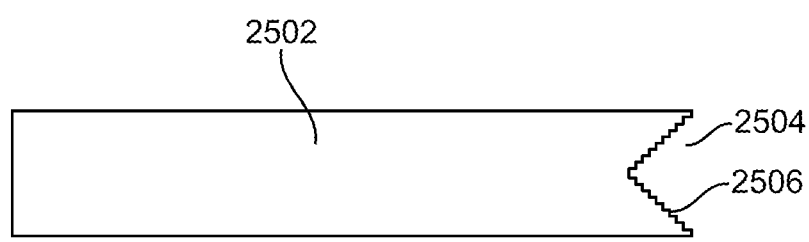
FIG. 25A shows a side view of an exemplary waveguide with optical surface features.
Figure 25B:
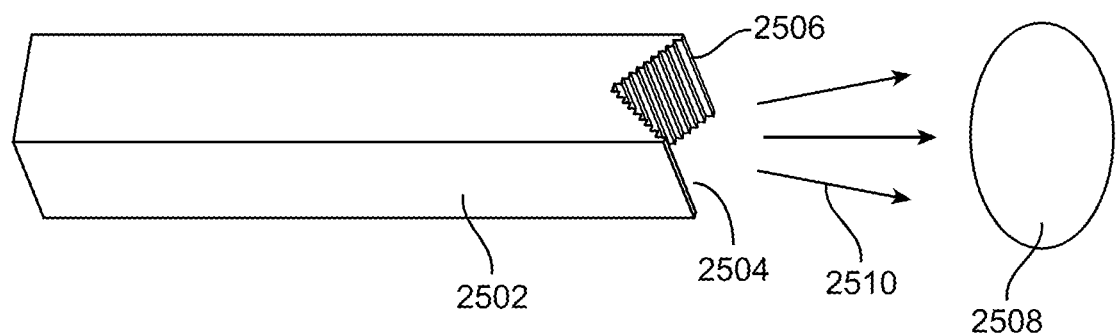
FIG. 25B shows a perspective view of the waveguide in FIG. 25A.

FIG. 25A illustrates another exemplary waveguide 2502 that may have a square or rectangular cross-section and a v-shaped recessed region 2504 at the distal end of the waveguide. The v-shaped recessed region includes two inner surfaces that are angled inwardly toward the proximal end of the waveguide, and may have surface features or microstructures along a part of or along the entire v-shaped recessed region. The microstructures may take the form of any of the microstructures discussed herein. In this embodiment, the microstructures form stair steps with a riser surface and a step surface that extract the light and control the extracted light to direct it to a target to be illuminated. FIG. 25B shows a perspective view of the waveguide in FIG. 25A with light 2510 emitted therefrom and forming a spot 2508 illuminating a target. Other aspects of the waveguide in FIGS. 25A-25B may take the same form as those previously discussed in FIGS. 23A-23B.

Figure 26:
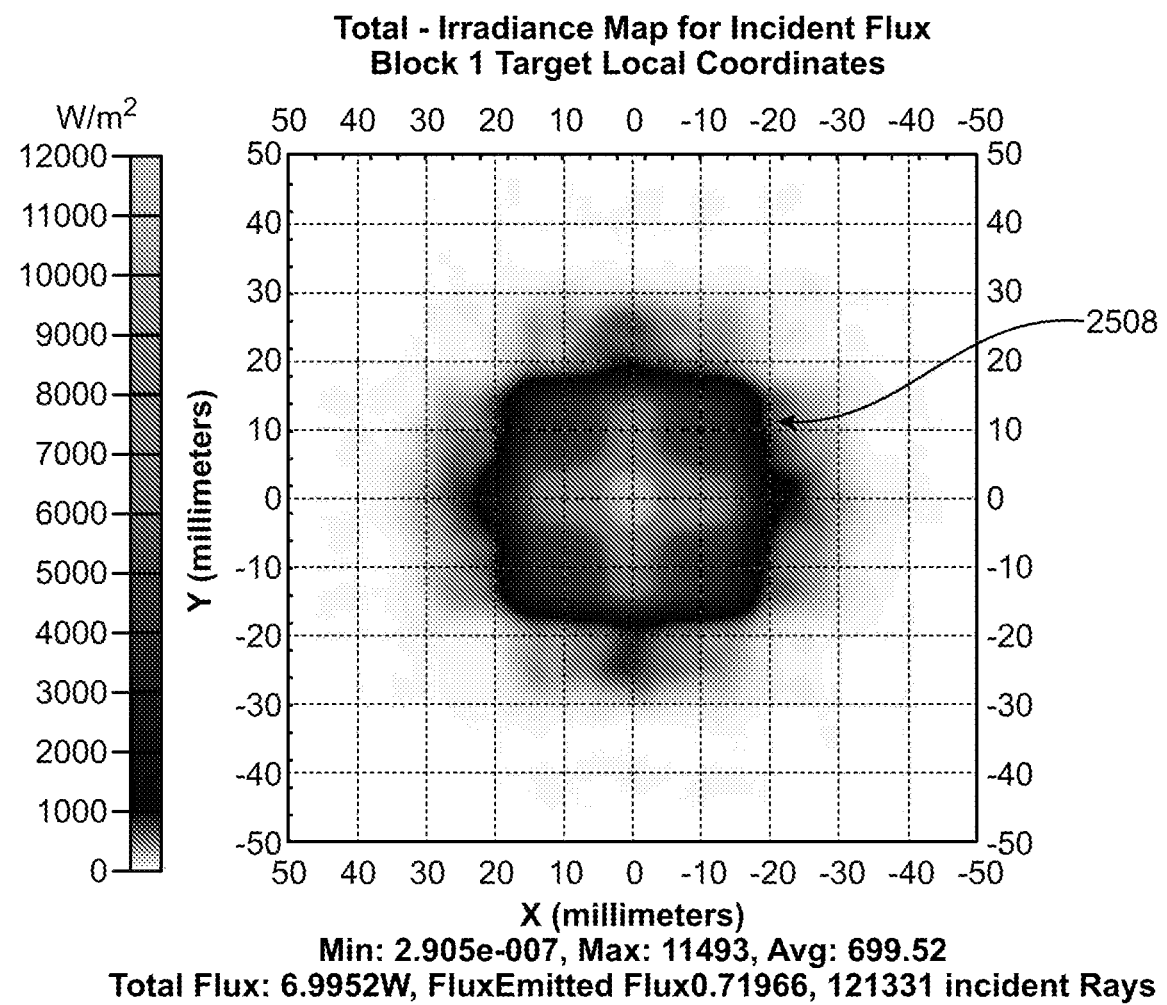
FIG. 26 illustrates an exemplary illumination spot provided by the waveguide in FIGS. 25A-25B.

FIG. 26 illustrates the spot of light 2508 that is preferably emitted by the waveguide having the microstructures illustrated in FIGS. 25A-25B. The spot 2508 is substantially similar to the spot 2308 in FIG. 24.

Figure 27A:
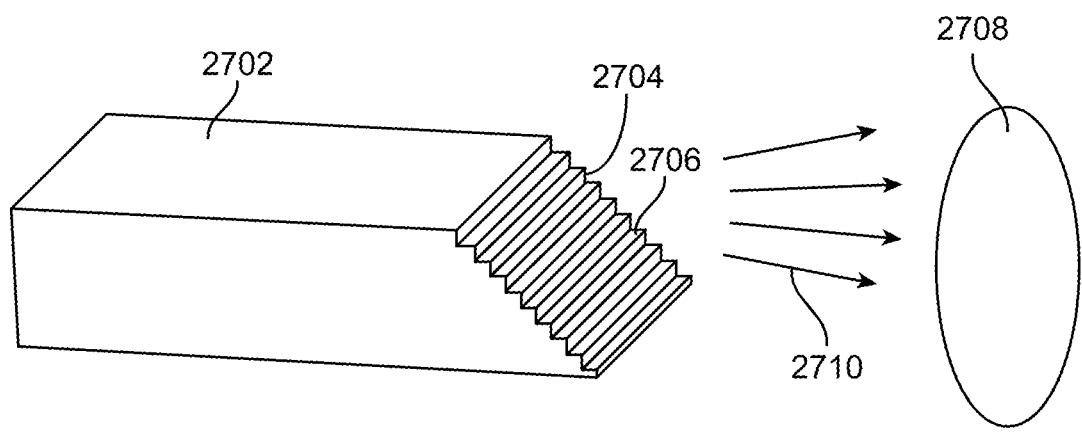
FIG. 27A shows a perspective view of an exemplary waveguide with optical surface features.
Figure 27B:
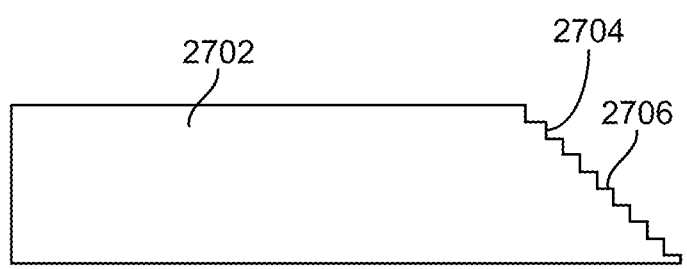
FIG. 27B shows a side view of the waveguide in FIG. 27A.

FIG. 27A shows still another exemplary embodiment of a waveguide 2702 with a rectangular or square cross-section and a ramped or angled distal surface 2704. Surface features 2706 such as stair steps may be disposed along a part of the outer ramped surface or along the entire ramped surface. The surface features may take the form of any of the other surface features disclosed herein. Light 2710 emitted from the surface features forms a spot 2708 that illuminates the target. FIG. 27B shows a side view of the waveguide in FIG. 27A. The device, surgical instrument, or other instrument is preferably coupled to the long side of the waveguide, although it may be coupled to any side.

Figure 28:
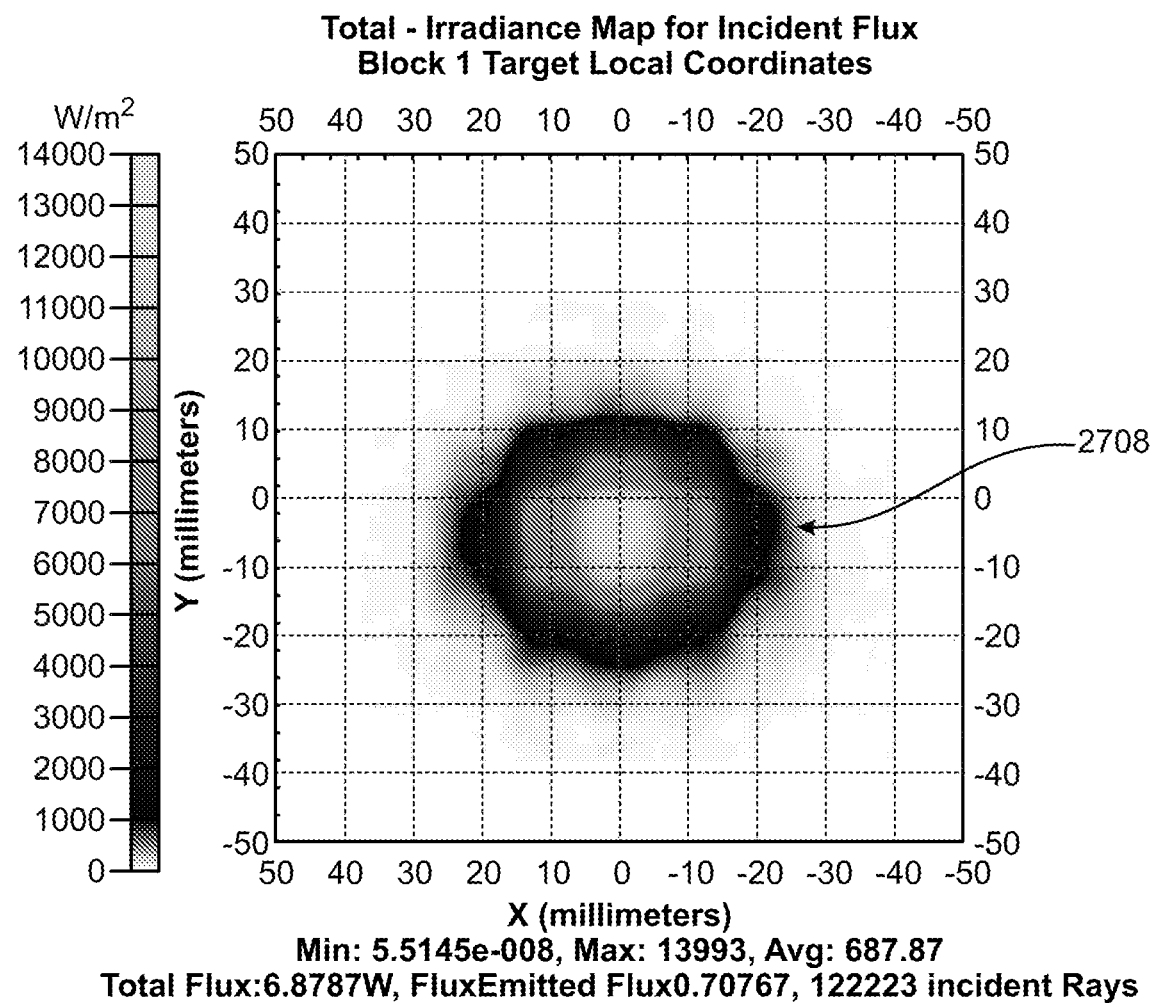
FIG. 28 shows an exemplary illumination spot provided by the waveguide in FIGS. 27A-27B.

FIG. 28 shows the spot 2708 that is preferably formed by the waveguide in FIGS. 27A-27B. The spot is still preferably rectangular, however because the waveguide may a greater width and greater height than the internal or externally wedges shaped waveguides previously discussed, the spot is more rectangular than square.

Figure 29A:
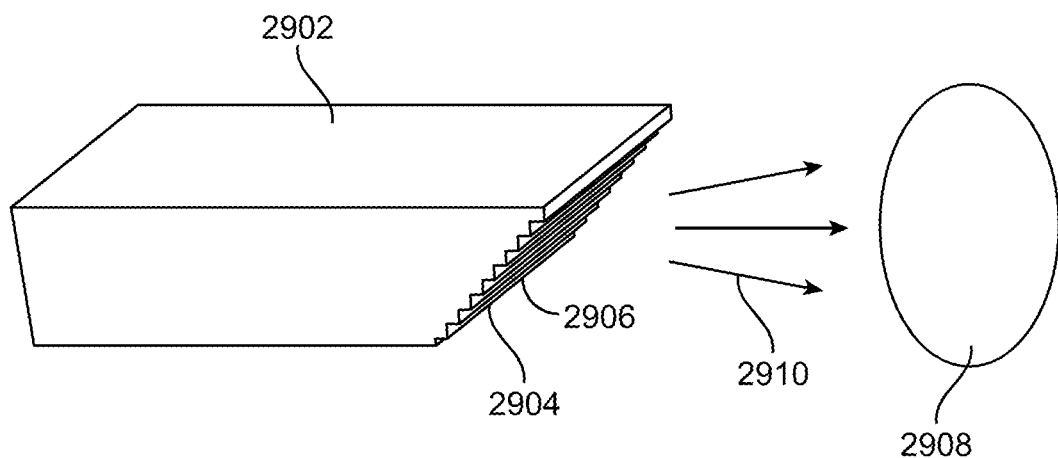
FIG. 29A shows a perspective view of an exemplary waveguide with optical features.

FIG. 29A illustrates a perspective view of yet another exemplary embodiment of a waveguide 2902 having surface features 2906 disposed on an angled ramp surface 2904. This embodiment is similar to that described in FIGS. 27A-27B with the major difference being that the ramp surface is now on the underside of the waveguide unlike the previous embodiment which had the ramp on the outer or upper surface of the ramp. The device, surgical instrument or other instrument is preferably coupled to the short side of the waveguide. Other aspects of this embodiment are generally the same as those described with respect to FIGS.

Figure 29B:
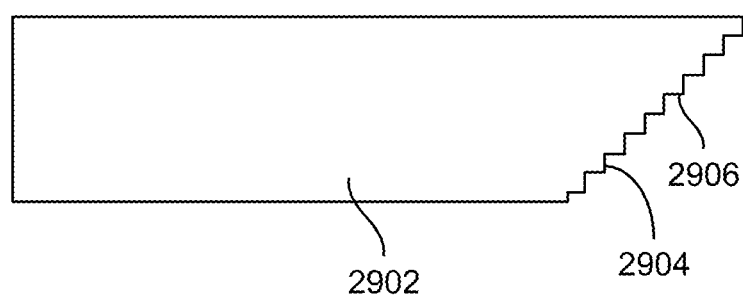
FIG. 29B shows a side view of the waveguide in FIG. 29A.

27A-27B. Light 2910 is emitted from the waveguide and forms a spot 2908 on the target. FIG. 29B shows a side view FIG. 29A.

Figure 30:
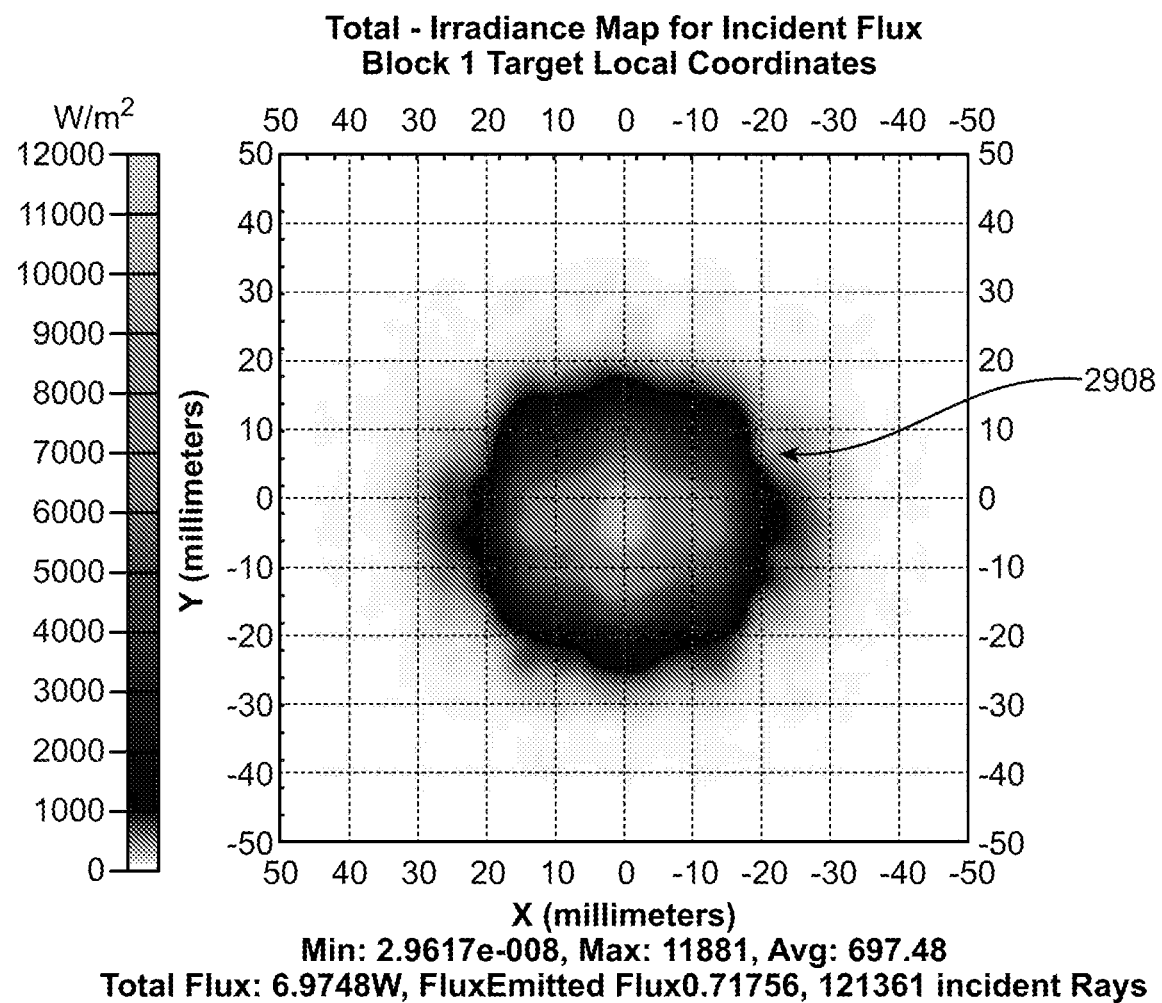
FIG. 30 shows an exemplary illumination spot provided by the waveguide in FIGS. 29A-29B.

FIG. 30 illustrates the illumination spot 2908 that is preferably formed by light emitted from the waveguide in FIGS. 29A-29B.

Figure 31:
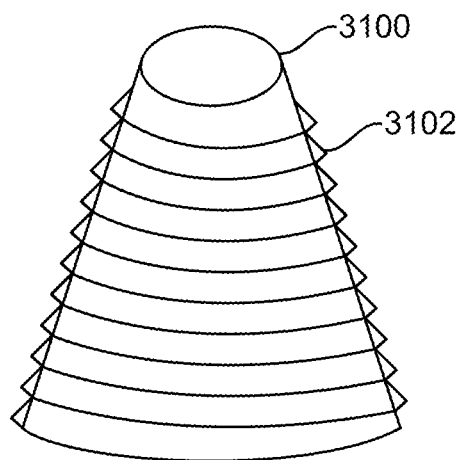
FIGS. 31-32 illustrate exemplary embodiments of surface features on the outer surface or inner surface of a waveguide.

FIG. 31 shows surface features 3102 on a conically shaped waveguide 3100. The surface features may be stair steps like those previously discussed, or any shaped may be used to extract the light from the waveguide and direct the extracted light to the target area to be illuminated.

Figure 32:
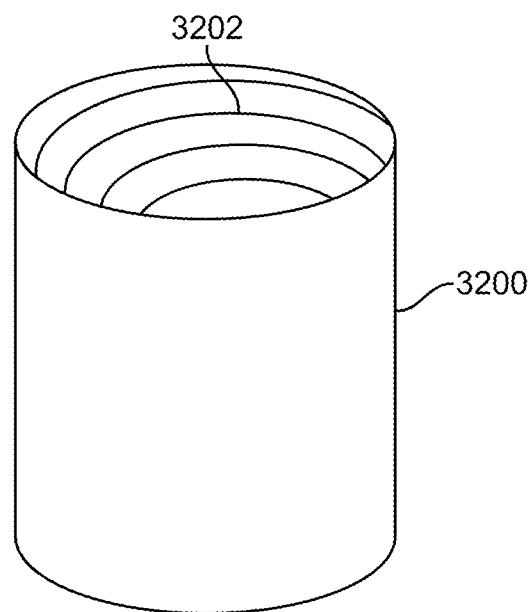

FIG. 32 shows another exemplary embodiment with a cylindrically shaped waveguide 3200 that has surface features 3202 disposed on an internal tapered surface of the waveguide. The surface features may be stair steps of any other shape needed in order to extract the light and direct it to the target.

The stair steps on any of the waveguides described herein may take any form or shape. Two optional embodiments which may be applied to any of the waveguides are illustrated in FIGS. 34A-34B.

Figure 34A:
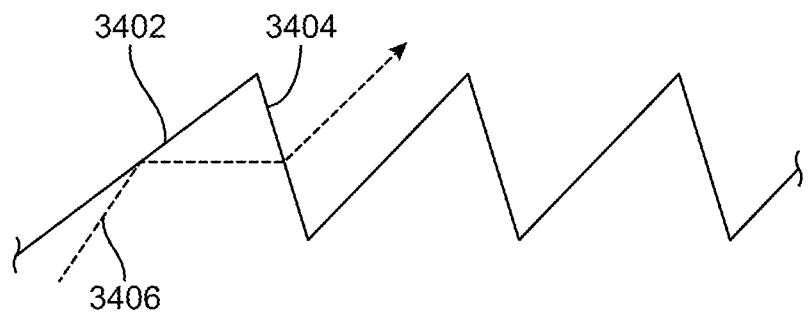
FIGS. 34A-34B illustrate exemplary embodiments of optical surface features on a waveguide.

FIG. 34A illustrates stair steps having a jagged saw toothed shape. A positive sloped ramped riser surface 3402 is angled to maximize total internal reflection of light hitting the ramped surface, and a negatively sloped ramp surface 3404 is angled to facilitate extraction of light from the waveguide. The path of a light ray 3406 through the waveguide is illustrated and shows the light refracted off the positively sloped ramp surface 3402 and then extracted from the negatively sloped surface 3404. The lengths of the positively sloped ramp surface and the negatively sloped ramp surface may change from step to step (e.g. increase or decrease in length) and similarly the angles of the positively sloped surface and the negatively sloped surface may also change from step to step, (e.g. increase or decrease in magnitude) in order to control the light. Optionally, the angle of the positively sloped surface relative to a horizontal line is acute, and optionally the angle of the negatively sloped surface is obtuse relative to a horizontal line, but this not intended to be limiting and any angle may be used.

Figure 34B:
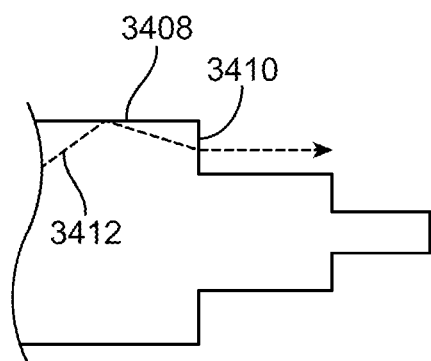

FIG. 34B illustrates stair steps having more horizontal and more vertical surfaces relative to the surfaces previously described in FIG. 34A. A more horizontal planar surface 3408 (sometime referred to as the riser surface) helps maintain total internal reflection of the light in the waveguide, and the more vertical planar surface 3410 extracts light from the waveguide and directs the light to the target. A ray of light 3412 shows the light refracted off of the flat planar surface 3408 and then extracted from the vertical surface 3410. The angles of the horizontal and vertical surfaces optionally may be zero and perpendicular, respectively relative to a horizontal line, but this is not intended to be limiting and any angle may be used.

Any of the waveguides described herein may be fabricated from multiple components coupled together (e.g. a D-shaped waveguide coupled to another D-shaped waveguide to produce a cylindrical waveguide), or the waveguide may be a single integral component that preferably has uniform material properties.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An illuminated surgical instrument, said illuminated surgical instrument comprising:
    a handheld surgical instrument selected from the group consisting of a suction tube, probe, an electrosurgery instrument, and a camera;
    a non-fiber optic optical waveguide coupled to the handheld surgical instrument, wherein the non-fiber optic optical waveguide comprises:
        a light input section at a proximal portion of the non-fiber optic optical waveguide, wherein the light input section is configured to input light into the non-fiber optic optical waveguide;
        a light transmitting section optically coupled to the light input section, and
        a light output section located distal of the light transmitting section, wherein the light transmitting section is configured to transmit the light from the light input section to the light output section, and
        a conical bore defined by the light output section,
        wherein, in a direction from a distal end of the non-fiber optic optical waveguide toward a proximal end of the non-fiber optic optical waveguide, the conical bore tapers inwardly such that a diameter of the conical bore reduces in size in the direction from the distal end toward the proximal end; and
    one or more spacers between the non-fiber optic optical waveguide and the handheld surgical instrument,
    wherein the one or more spacers are configured to define an air gap between the non-fiber optic optical waveguide and the handheld surgical instrument,
    wherein the distal end of the non-fiber optic optical waveguide is offset proximally from a distal end of the handheld surgical instrument.

2. The illuminated surgical instrument of claim 1, further comprising a plurality of surface features on an inner wall of the conical bore, wherein the plurality of surface features are selected from the group consisting of: stair steps, prisms, microstructures, radiused facets, planar facets, and lenslets.

3. The illuminated surgical instrument of claim 1, wherein the light extracted from the light output section has an energy density, and wherein the light output section has an extraction area large enough to maintain the energy density at a level that prevents temperature exceeding a glass transition temperature of the illuminated surgical instrument.

4. The illuminated surgical instrument of claim 1, wherein the handheld surgical instrument comprises a suction tube, and a suction control mechanism fluidly coupled to the suction tube.

5. The illuminated surgical instrument of claim 1, wherein light is transmitted through the light transmitting section by total internal refection (TIR).

6. A method for illuminating a surgical field in a patient, said method comprising:
    providing an illuminated surgical instrument according to claim 1;
    inputting light from a light source into the non-fiber optic optical waveguide via the light input section;
    transmitting the light through the light transmitting section;
    extracting the light from the conical bore defined by the light output section; and illuminating the surgical field with the light that is extracted from the conical bore defined by the light output section.

7. The illuminated surgical instrument of claim 1, further comprising an outer cladding on an outer surface of the non-fiber optic optical waveguide.

8. The illuminated surgical instrument of claim 7, wherein the outer cladding has an index of refraction in a range from 1 to 1.5.

9. The illuminated surgical instrument of claim 1, wherein the non-fiber optic optical waveguide comprises a through bore extending from the conical bore to the proximal end of the non-fiber optic optical waveguide, and
wherein the handheld surgical instrument extends through the through bore and the conical bore of the non-fiber optic optical waveguide.

10. The illuminated surgical instrument of claim 9, wherein the non-fiber optic optical waveguide is concentric with the handheld surgical instrument.

11. The illuminated surgical instrument of claim 2, wherein the plurality of surface features comprise a plurality of the stair steps, and
wherein each stair step is formed into the conical bore of the non-fiber optic optical waveguide.

12. The illuminated surgical instrument of claim 11, wherein each stair step comprises a riser surface and a step surface, and
wherein each riser surface extends between adjacent step surfaces.

13. The illuminated surgical instrument of claim 2, wherein each surface feature extends around an entire circumference of the conical bore.

14. The illuminated surgical instrument of claim 2, wherein a first portion of the plurality of surface features extends entirely around a circumference of the conical bore, and a second portion of the plurality of surface features extends only partially around the circumference of the conical bore.

15. The illuminated surgical instrument of claim 14, wherein one side of the conical bore has a greater quantity of the plurality of surface features than another side of the conical bore.

16. The illuminated surgical instrument of claim 14, wherein the first portion of the plurality of surface features are positioned distal of the second portion of the plurality of surface features on the conical bore.

17. The illuminated surgical instrument of claim 14, wherein each surface feature of the second portion partially extends around the circumference by a respective circumferential distance, and
wherein the respective circumferential distances of the second portion of the plurality of surface features decreases in a proximal direction.

18. The illuminated surgical instrument of claim 1, further comprising an inner cladding material between the non-fiber optic optical waveguide and the handheld surgical instrument.

19. The illuminated surgical instrument of claim 1, further comprising a protective cover at the distal end of the non-fiber optic optical waveguide, wherein the protective cover is configured to inhibit the conical bore from contact with blood or tissue.

* * * * *